US006610493B1

(12) United States Patent
Citron et al.

(10) Patent No.: US 6,610,493 B1
(45) Date of Patent: *Aug. 26, 2003

(54) SCREENING COMPOUNDS FOR THE ABILITY TO ALTER THE PRODUCTION OF AMYLOID-β PEPTIDE

(75) Inventors: Martin Citron, Thousands Oaks, CA (US); Dennis J. Selkoe, Jamaica Plain, MA (US); Peter A. Seubert, San Francisco, CA (US); Dale Schenk, Burlingame, CA (US)

(73) Assignees: Brigham and Women's Hospital, Boston, MA (US); Athena Neurosciences, Inc., South San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/665,649

(22) Filed: Jun. 18, 1996

Related U.S. Application Data

(63) Continuation-in-part of application No. 08/079,511, filed on Jun. 17, 1993, now Pat. No. 5,766,846.

(51) Int. Cl.$^7$ .............................................. G01N 33/53
(52) U.S. Cl. ........................ 435/7.1; 435/7.2; 435/7.21; 435/7.23; 435/7.8; 435/7.92
(58) Field of Search ........................ 435/7.1, 7.2, 7.21, 435/7.23, 7.8, 7.92; 530/387.1

(56) References Cited

U.S. PATENT DOCUMENTS

| 4,271,140 A | | 6/1981 | Bunting |
| 4,666,829 A | | 5/1987 | Glenner et al. |
| 5,387,742 A | | 2/1995 | Cordell |
| 5,750,349 A | * | 5/1998 | Suzuki et al. |

FOREIGN PATENT DOCUMENTS

| WO | WO 93/14200 | 7/1993 |

OTHER PUBLICATIONS

Tamaoka et al *Neurobiology of Aging* 17(3) pp. 405–414 (1996).*
Asami–Odaka et al. (1995) *Biochemistry* 34:10272–10278.
Buxbaum et al. (1993) *Proc. Natl. Acad. Sci. USA* 90:9195–9198.
Chartier–Harlin et al. (1991) *Nature* 353:844–846.
Chui et al., *Archive of Neurology* 50(1):57–63, Jan. 1993.
Citron et al. (1992) *Nature* 360:672–674.
Dovey et al. (1993) *NeuroReport* 4:1039–1042.
Fukuchi et al., *Annals of the New York Academy of Sciences*, 695:217–223, 1993.
Games et al., *Nature*, 373:523–527, Feb. 9, 1995.
Glenner and Wong (1984) *Biochem. Biophys. Res. Commun.* 120:885–890.
Goate et al. (1991) *Nature* 349:704–706.
Gravina et al. (1995) *J. Biol. Chem.* 270:7013–7016.
Haass et al. (1995) *Nature Med.* 1:1291–1296.
Haass et al. (1994) *J. Biol. Chem.* 269:17741–17748.
Haass et al. (1992) *Nature* 359:322–325.
Hardy (1992) *Nature Genet.* 1:233–234.
Higaki et al. (1995) *Neuron* 14:651–659.
Hung et al. (1993) *J. Biol. Chem.* 268:22959–22962.
Iwatsubo et al. (1995) *Ann. Neurol.* 37:294–299.
Iwatsubo et al., *Neuron*, 13:45–53, Jul. 1994.
Jarrett et al. (1993) *Biochemistry* 32:4693–4697.
Kang et al. (1987) *Nature* 325:733–736.
Kitaguchi et al. (1988) *Nature* 331:530–532.
Knops et al. (1995) *J. Biol. Chem.* 270:2419–2422.
Koo and Squazzo (1994) *J. Biol. Chem.* 269:17386–17389.
Lannfelt et al., *Behavorial Brain Research*, 57:207–213, 1993.
Lemere et al. (1996) *Neurology of Diseases* 3:16–32.
Mullan et al. (1992) *Nature Genet* 1:345–347.
Murrell et al. (1991) *Science* 254:97–991.
Oltersdorf (1990) *J. Biol. Chem.* 265:4492–4497.
Podlisny et al. (1981) *Am. J. Pathol.* 138:1423–1435.
Ponte et al. (1988) *Nature* 331:525–527.
Roher et al. (1993) *Proc. Natl. Acad. Sci. USA* 90:10836–840.
Saido et al. (1994) *J. Biol. Chem.* 269:15253–15257.
Schenk et al. (1995) *J. Med. Chem.* 38:4141–4154.
Scheuner et al., *Nature Medicine*, 2(8):864–870, 1996.
Scheuner et al. (1995) *Neurosci. Abstracts* in press.
Selkoe (1994) *J. Neuropath. and Exp. Neurol.* 53:438–447.
Selkoe et al. (1988) *Proc. Natl. Acad. Sci. USA* 85:7341–7345.
Selkoe (1991) *Neuron* 6:487–498.
Seubert et al. (1992) *Nature* 359:325–327.
Suzuki et al. (1994) *Science* 264:1336–1340.
Tanzi et al. (1988) *Nature* 331:528–530.
Ueda et al., *The Journal of Neuroscience*, 10(10):3295–3304, Oct. 1990.
Uno et al., *Annals of the New York Academy of Sciences*, 695:232–235, 1993.
Vigo–Pelfrey et al. (1993) *J. Neurochem.* 61:1965–68.
Annals of Neurology, vol. 22, No. 4, issued Oct. 1987, Wolozin et al., "Alzheimer–Related Neuronal Protein A68:Specificity and Distribution", pp. 521–526.

* cited by examiner

*Primary Examiner*—Patricia A. Duffy
(74) *Attorney, Agent, or Firm*—Townsend and Townsend and Crew LLP

(57) ABSTRACT

This invention provides methods of screening compounds for their ability to alter the production of Aβ(x≧41) alone or in combination with Aβ(x≦40). The methods involve administering compounds to cells, specifically measuring the amounts of Aβ(x≦40) and Aβ(x≧41) produced by the cells, and comparing these amounts to that produced by the cells without administration of the compounds.

21 Claims, 26 Drawing Sheets

(2) INFORMATION FOR SEQ ID NO:5:
   (i) SEQUENCE CHARACTERISTICS:
      (A) LENGTH: 2310 base pairs
      (B) TYPE: nucleic acid
      (C) STRANDEDNESS: double
      (D) TOPOLOGY: linear
   (ii) MOLECULE TYPE: cDNA
   (iii) HYPOTHETICAL: NO
   (iv) ANTI-SENSE: NO
   (ix) FEATURE:
      (A) NAME/KEY: CDS
      (B) LOCATION: 1-2310
      (D) OTHER INFORMATION: /function= "coding region for APP770."
   (xi) SEQUENCE DESCRIPTION: SEQ ID NO:5:

```
ATG CTG CCC GGT TTG GCA CTG CTG CTC CTG GCC GCC TGG ACG GCT CGG    48
Met Leu Pro Gly Leu Ala Leu Leu Leu Leu Ala Ala Trp Thr Ala Arg
 1               5                  10                  15

GCG CTG GAG GTA CCC ACT GAT GGT AAT GCT GGC CTG CTG GCT GAA CCC    96
Ala Leu Glu Val Pro Thr Asp Gly Asn Ala Gly Leu Leu Ala Glu Pro
             20                  25                  30

CAG ATT GCC ATG TTC TGT GGC AGA CTG AAC ATG CAC ATG AAT GTC CAG   144
Gln Ile Ala Met Phe Cys Gly Arg Leu Asn Met His Met Asn Val Gln
         35                  40                  45

AAT GGG AAG TGG GAT TCA GAT CCA TCA GGG ACC AAA ACC TGC ATT GAT   192
Asn Gly Lys Trp Asp Ser Asp Pro Ser Gly Thr Lys Thr Cys Ile Asp
 50                  55                  60
```

FIG. 10A.

```
ACC AAG GAA GGC ATC CTG CAG TAT TGC CAA GAA GTC TAC CCT GAA CTG       240
Thr Lys Glu Gly Ile Leu Gln Tyr Cys Gln Glu Val Tyr Pro Glu Leu
 65                  70                  75                  80

CAG ATC ACC AAT GTG GTA GAA GCC AAC CAA CCA GTG ACC ATC CAG AAC       288
Gln Ile Thr Asn Val Val Glu Ala Asn Gln Pro Val Thr Ile Gln Asn
                 85                  90                  95

TGG TGC AAG CGG GGC CGC AAG CAG TGC AAG ACC CAT CCC CAC TTT GTG       336
Trp Cys Lys Arg Gly Arg Lys Gln Cys Lys Thr His Pro His Phe Val
100                 105                 110

ATT CCC TAC CGC TGC TTA GTT GGT GAG TTT GTA AGT GAT GCC CTT CTC       384
Ile Pro Tyr Arg Cys Leu Val Gly Glu Phe Val Ser Asp Ala Leu Leu
        115                 120                 125

GTT CCT GAC AAG TGC AAA TTC TTA CAC CAG GAG AGG ATG GAT GTT TGC       432
Val Pro Asp Lys Cys Lys Phe Leu His Gln Glu Arg Met Asp Val Cys
130                 135                 140

GAA ACT CAT CTT CAC TGG CAC ACC GTC GCC AAA GAG ACA TGC AGT GAG       480
Glu Thr His Leu His Trp His Thr Val Ala Lys Glu Thr Cys Ser Glu
145                 150                 155                 160

AAG AGT ACC AAC TTG CAT GAC TAC GGC ATG TTG CTG CCC TGC GGA ATT       528
Lys Ser Thr Asn Leu His Asp Tyr Gly Met Leu Leu Pro Cys Gly Ile
        165                 170                 175
```

FIG. 10B.

```
GAC AAG TTC CGA GGG GTA GAG TTT GTG TGT TGC CCA CTG GCT GAA GAA    576
Asp Lys Phe Arg Gly Val Glu Phe Val Cys Cys Pro Leu Ala Glu Glu
        180                 185                 190

AGT GAC AAT GTG GAT TCT GCT GAT GCG GAG GAG GAT GAC TCG GAT GTC    624
Ser Asp Asn Val Asp Ser Ala Asp Ala Glu Glu Asp Asp Ser Asp Val
        195                 200                 205

TGG TGG GGC GGA GCA GAC ACA GAC TAT GCA GAT GGG AGT GAA GAC AAA    672
Trp Trp Gly Gly Ala Asp Thr Asp Tyr Ala Asp Gly Ser Glu Asp Lys
        210                 215                 220

GTA GTA GAA GTA GCA GAG GAG GAA GAA GTG GCT GAG GTG GAA GAA GAA    720
Val Val Glu Val Ala Glu Glu Glu Glu Val Ala Glu Val Glu Glu Glu
        225                 230                 235                 240

GAA GCC GAT GAT GAT GAG GAC GAT GAG GAT GGT GAT GAG GTA GAG GAA    768
Glu Ala Asp Asp Asp Glu Asp Asp Glu Asp Gly Asp Glu Val Glu Glu
        245                 250                 255

GAG GCT GAG GAA CCC TAC GAA GAA GCC ACA GAG AGA ACC ACC AGC ATT    816
Glu Ala Glu Glu Pro Tyr Glu Glu Ala Thr Glu Arg Thr Thr Ser Ile
        260                 265                 270

GCC ACC ACC ACC ACC ACC ACC ACA ACC ACA GAG TCT GTG GAA GAG GTG GTT CGA    864
Ala Thr Thr Thr Thr Thr Thr Thr Thr Thr Glu Ser Val Glu Glu Val Val Arg
        275                 280                 285
```

FIG. 10C.

```
GAG GTG TGC TCT GAA CAA GCC GAG ACG GGG CCG TGC CGA GCA ATG ATC    912
Glu Val Cys Ser Glu Gln Ala Glu Thr Gly Pro Cys Arg Ala Met Ile
290             295                 300

TCC CGC TGG TAC TTT GAT GTG ACT GAA GGG AAG TGT GCC CCA TTC TTT    960
Ser Arg Trp Tyr Phe Asp Val Thr Glu Gly Lys Cys Ala Pro Phe Phe
305             310                 315                 320

TAC GGC GGA TGT GGC GGG AAC CGG AAC AAC TTT GAC ACA GAA GAG TAC   1008
Tyr Gly Gly Cys Gly Gly Asn Arg Asn Asn Phe Asp Thr Glu Glu Tyr
            325                 330                 335

TGC ATG GCC GTG TGT GGC AGC GCC ATG TCC CAA AGT TTA CTC AAG ACT   1056
Cys Met Ala Val Cys Gly Ser Ala Met Ser Gln Ser Leu Leu Lys Thr
340                 345                 350

ACC CAG GAA CCT CTT GCC CGA GAT GCC CCT GTT AAA CTT CCT ACA GCA   1104
Thr Gln Glu Pro Leu Ala Arg Asp Ala Pro Val Lys Leu Pro Thr Ala
        355                 360                 365

GCC AGT ACC CCT GAT GCC GTT GAC AAG TAT CTC GAG ACA CCT GGG GAT   1152
Ala Ser Thr Pro Asp Ala Val Asp Lys Tyr Leu Glu Thr Pro Gly Asp
370                 375                 380

GAG AAT GAA CAT GCC CAT TTC CAG AAA GCC AAA GAG AGG CTT GAG GCC   1200
Glu Asn Glu His Ala His Phe Gln Lys Ala Lys Glu Arg Leu Glu Ala
385                 390                 395                 400
```

FIG. 10D.

| | | | | | | | | | | | | | | | |
|---|---|---|---|---|---|---|---|---|---|---|---|---|---|---|---|
| AAG | CAC | CGA | GAG | AGA | ATG | TCC | CAG | GTC | ATG | AGA | GAA | TGG | GAA | GAG | GCA |
| Lys | His | Arg | Glu | Arg | Met | Ser | Gln | Val | Met | Arg | Glu | Trp | Glu | Ala | |
| | | | 405 | | | | | | 410 | | | | | 415 | |

1248

| GAA | CGT | CAA | GCA | AAG | AAC | TTG | CCT | AAA | GCT | GAT | AAG | AAG | GCA | GTT | ATC |
|---|---|---|---|---|---|---|---|---|---|---|---|---|---|---|---|
| Glu | Arg | Gln | Ala | Lys | Asn | Leu | Pro | Lys | Ala | Asp | Lys | Lys | Ala | Val | Ile |
| | | 420 | | | | | 425 | | | | | 430 | | | |

1296

| CAG | CAT | TTC | CAG | GAG | AAA | GTG | GAA | TCT | TTG | GAA | CAG | GAA | GCA | GCC | AAC |
|---|---|---|---|---|---|---|---|---|---|---|---|---|---|---|---|
| Gln | His | Phe | Gln | Glu | Lys | Val | Glu | Ser | Leu | Glu | Gln | Glu | Ala | Ala | Asn |
| | 435 | | | | | 440 | | | | | 445 | | | | |

1344

| GAG | AGA | CAG | CAG | CTG | GTG | GAG | ACA | CAC | ATGGCC | AGA | GTG | GAA | GCC | ATG |
|---|---|---|---|---|---|---|---|---|---|---|---|---|---|---|
| Glu | Arg | Gln | Gln | Leu | Val | Glu | Thr | His | Met Ala | Arg | Val | Glu | Ala | Met |
| 450 | | | | | 455 | | | | 460 | | | | | |

1392

| CTC | AAT | GAC | CGC | CGC | CGC | CTG | GCC | CTG | GAG | AAC | TAC | ATC | ACC | GCT | CTG |
|---|---|---|---|---|---|---|---|---|---|---|---|---|---|---|---|
| Leu | Asn | Asp | Arg | Arg | Arg | Leu | Ala | Leu | Glu | Asn | Tyr | Ile | Thr | Ala | Leu |
| 465 | | | | | 470 | | | | | 475 | | | | | 480 |

1440

| CAG | GCT | GTT | CCT | CCT | CGG | CCT | CGT | CAC | GTG | TTC | AAT | ATG | CTA | AAG | AAG |
|---|---|---|---|---|---|---|---|---|---|---|---|---|---|---|---|
| Gln | Ala | Val | Pro | Pro | Arg | Pro | Arg | His | Val | Phe | Asn | Met | Leu | Lys | Lys |
| | | | 485 | | | | | 490 | | | | | 495 | | |

1488

| TAT | GTC | CGC | GCA | GAA | CAG | AAG | GAC | AGA | CAG | CAC | ACC | CTA | AAG | CAT | TTC |
|---|---|---|---|---|---|---|---|---|---|---|---|---|---|---|---|
| Tyr | Val | Arg | Ala | Glu | Gln | Lys | Asp | Arg | Gln | His | Thr | Leu | Lys | His | Phe |
| | | 500 | | | | | 505 | | | | | 510 | | | |

```
GAG CAT GTG CGC ATG GTG GAT CCC AAG AAA GCC CAG ATC CGG TCC     1584
Glu His Val Arg Met Val Asp Pro Lys Lys Ala Gln Ile Arg Ser
        515                 520                 525

CAG GTT ATG ACA CAC CTC CGT GTG ATT TAT GAG CGC ATG AAT CAG TCT 1632
Gln Val Met Thr His Leu Arg Val Ile Tyr Glu Arg Met Asn Gln Ser
        530                 535                 540

CTC TCC CTG TAC AAC GTG CCT GCA GTG GCC GAG GAG ATT CAG GAT     1680
Leu Ser Leu Tyr Asn Val Pro Ala Val Ala Glu Glu Ile Gln Asp
        545                 550                 555         560

GAA GTT GAT GAG CTG CTT CAG AAA GAG CAA AAC TAT TCA GAT GAC GTC 1728
Glu Val Asp Glu Leu Leu Gln Lys Glu Gln Asn Tyr Ser Asp Asp Val
        565                 570                 575

TTG GCC AAC ATG ATT AGT GAA CCA AGG ATC AGT TAC GGA AAC GAT GCT 1776
Leu Ala Asn Met Ile Ser Glu Pro Arg Ile Ser Tyr Gly Asn Asp Ala
        580                 585                 590

CTC ATG CCA TCT TTG ACC GAA ACG AAA ACC ACC GTG GAG CTC CTT CCC 1824
Leu Met Pro Ser Leu Thr Glu Thr Lys Thr Thr Val Glu Leu Leu Pro
        595                 600                 605

GTG AAT GGA GAG TTC AGC CTG GAC GAT CTC CAG CCG TGG CAT TCT TTT 1872
Val Asn Gly Glu Phe Ser Leu Asp Asp Leu Gln Pro Trp His Ser Phe
        610                 615                 620
```

*FIG. 10F.*

```
GGG GCT TCT GTG CCA GCC AAC ACA GAA AAC GAA GTT GAG CCT GTT    1920
Gly Ala Ser Val Pro Ala Asn Thr Glu Asn Glu Val Glu Pro Val
625                 630                 635                 640

GAT GCC CGC CCT GCT GCC GAC GGA CTG CGA GGA CGG CCA GGT TCT    1968
Asp Ala Arg Pro Ala Ala Asp Arg Gly Leu Thr Thr Arg Pro Gly Ser
            645                 650                 655

GGG TTG ACA AAT ATC AAG ACG GAG GAG ATC TCT GAA GTG AAG ATG GAT 2016
Gly Leu Thr Asn Ile Lys Thr Glu Glu Ile Ser Glu Val Lys Met Asp
        660                 665                 670

GCA GAA TTC CGA CAT GAC TCA GGA TAT GAA GTT CAT CAT CAA AAA TTG 2064
Ala Glu Phe Arg His Asp Ser Gly Tyr Glu Val His His Gln Lys Leu
    675                 680                 685

GTG TTC TTT GCA GAA GAT GTG GGT TCA AAC AAA GGT GDA ATC ATT GGA 2112
Val Phe Phe Ala Glu Asp Val Gly Ser Asn Lys Gly Ala Ile Ile Gly
690                 695                 700

CTC ATG GTG GGC GGT GTT GTC ATA GCG ACA GTG ATC GTC ATC ACC TTG 2160
Leu Met Val Gly Gly Val Val Ile Ala Thr Val Ile Val Ile Thr Leu
705                 710                 715                 720

GTG ATG CTG AAG AAA CAG TAC ACA TCC ATT CAT CAT GGT GTG GTG    2208
Val Met Leu Lys Lys Lys Gln Tyr Thr Ser Ile His His Gly Val Val
            725                 730                 735
```

FIG. 10G.

GAG GTT GAC GCC GCT GTC ACC CCA GAG GAG CGC CAC CTG TCC AAG ATG    2256
Glu Val Asp Ala Ala Val Thr Pro Glu Glu Arg His Leu Ser Lys Met
              740                 745                 750

CAG CAG AAC GGC TAC GAA AAT CCA ACC TAC AAG TTC TTT GAG CAG ATG    2304
Gln Gln Asn Gly Tyr Glu Asn Pro Thr Tyr Lys Phe Phe Glu Gln Met
              755                 760                 765

CAG AAC                                                            2310
Gln Asn
  770

FIG. 10H.

SCREENING COMPOUNDS FOR THE ABILITY TO ALTER THE PRODUCTION OF AMYLOID-β PEPTIDE

This application is a continuation in part of United States application Ser. No. 8/079,511, filed Jun. 17, 1993, now U.S. Pat. No. 5,766,846.

This invention was made in part with Government support under grant no. 2 P50 AG05134 awarded by the National Institutes of Health. The Government may have rights in this invention.

BACKGROUND OF THE INVENTION

1. Field of the Invention

The present invention relates generally to neurology and, more particularly, to assays, such as immunoassays, for screening for compounds that specifically alter the production of various isoforms of Aβ.

Alzheimer's disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in all races and ethnic groups worldwide and presents a major present and future public health problem. The disease is currently estimated to affect about two to three million individuals in the United States alone. AD is at present incurable. No treatment that effectively prevents AD or reverses its symptoms or course is currently known.

The brains of individuals with AD exhibit characteristic lesions termed senile plaques and neurofibrillary tangles. Large numbers of these lesions are generally found in patients with AD in several areas of the human brain important for memory and cognitive function. Smaller numbers of these lesions in a more restricted anatomical distribution are sometimes found in the brains of aged humans who do not have clinical AD. Senile plaques and vascular amyloid deposits (amyloid angiopathy) also characterize the brains of individuals beyond a certain age with Trisomy 21 (Down's Syndrome) and Hereditary Cerebral Hemorrhage with Amyloidosis of the Dutch-Type (HCHWA-D). The principal chemical constituent of the senile plaques and vascular amyloid deposits characteristic of AD and the other disorders mentioned above is a protein designated the amyloid-β peptide (Aβ) or sometimes βAP, AβP or β/A4. Aβ was first purified and a partial amino acid sequence reported in Glenner and Wong (1984) *Biochem. Biophys. Res. Commun.* 120:885–890. The isolation procedure and the sequence data for the first 28 amino acids are described in U.S. Pat. No. 4,666,829. Forms of Aβ having amino acids beyond number 40 were first reported by Kang et al. (1987) *Nature* 325:733–736.

Roher et al. (1993) *Proc. Natl. Acad. Sci. USA* 90:10836–840 showed that Aβ(1–42) is the major constituent in neuritic plaques, including significant amounts of isomerized and racemized aspartyl residues as their $NH_2$- termini. The authors also reported that Aβ(17–42) (p3(42)) predominates in diffuse (early) plaques, whereas Aβ(1–40) is the major constituent in the meningeal vessel deposits, comprising 60% of the total Aβ in those vessels. Iwatsubo et al. (1994) *Neuron* 13:45–53 showed that Aβ42(43)- containing senile plaques are the major species of senile plaques in sporadic AD brains. Iwatsubo et al. (1995) *Annals of Neurology* 37:294–299 and Lemere et al. (1996) *Neurobiology of Disease* 3:16–32 reported that Aβ42(43) is the major constituent of senile plaques in Down's syndrome brains and is the initially deposited Aβ species in the development of AD-type neuropathological legions in these patients. In addition, Gravina et al., (1995) *J. Biol. Chem.* 270:7013–7016 reported both biochemical and immunocytochemical evidence that Aβ42(43) peptides were the most abundant constituents of senile plaques in AD brains and exceeded the amounts of Aβ40 peptides in such plaques.

Molecular biological and protein chemical analyses conducted during the last several years have shown that Aβ is a small fragment of a much larger precursor protein, referred to as the β-amyloid precursor protein (APP), that is normally produced by cells in many tissues of various animals, including humans. Knowledge of the structure of the gene encoding APP has demonstrated that Aβ arises as a peptide fragment that is cleaved from the carboxy-terminal end of APP by as-yet-unknown enzymes (proteases). The precise biochemical mechanism by which the Aβ fragment is cleaved from APP and subsequently deposited as amyloid plaques in the cerebral tissue and in the walls of cerebral and meningeal blood vessels is currently unknown. Importantly, Haass et al. (*Nature* 359:322–325) and Seubert et al. ((1992) *Nature* 359:325–327) discovered that essentially all cells expressing the APP gene normally secrete an array of Aβ peptides, and these peptides can readily be detected and assayed in cell culture fluid (conditioned media) and human biological fluids such as plasma and cerebrospinal fluid. It has subsequently been shown that these fluids contain both the more abundant Aβ40-ending peptides and the less abundant Aβ42(43)-ending peptides (Dovey et al. (1993) *Neuroreport* 4:1039–1042 and Vigo-Pelfrey et al. (1993) *J. Neurochem.* 61:1965–68).

Several lines of evidence indicate that progressive cerebral deposition of Aβ plays a seminal role in the pathogenesis of AD and can precede cognitive symptoms by years or decades (for review, see Schenk (1995) *J. Med. Chem.* 38:4141–4154, Selkoe (1994) *J. Neuropath. and Exp. Neurol.* 53:438–447 and Selkoe (1991) *Neuron* 6:487). One of the most important lines of evidence is the discovery in 1991 that missense DNA mutations in the APP gene at amino acid 717 of the 770-amino acid isoform of APP can be found in affected members but not unaffected members of several families with a genetically determined (familial) form of AD (Goate et al. (1991) *Nature* 349:704–706; Chartier Harlan et al. (1991) *Nature* 353:844–846; and Murrell et al. (1991) *Science* 254:97–99). Suzuki et al. (1994) "An increased percentage of long amyloid β-protein secreted by familial amyloid β-protein precursor (βAPP717) mutants," *Science* 264:1336–1340 subsequently showed that, compared to normal individuals, the 717 mutation causes a higher relative production of the Aβ(1–42) peptide. In addition, a double mutation changing lysine$^{670}$-methionine$^{671}$ to asparagine$^{670}$-leucine$^{671}$ (with reference to the 770 isoform of APP) was reported in a Swedish family with familial AD in 1992 (Mullan et al. (1992) *Nature Genet* 1:345–347) and is referred to as the Swedish APP variant.

Genetic linkage analyses have demonstrated that the aforementioned mutations are the specific molecular cause of AD in the members of such families that carry these mutant APP genes. In addition, a mutation at amino acid 693 of the 770-amino acid isoform of APP has been identified as the cause of the Aβ deposition disease, Hereditary Cerebral Hemorrhage With Amyloidosis Dutch type (HCHWA-D), and a mutation from alanine to glycine at amino acid 692 appears to cause the phenotype of AD in some family members and the phenotype of HCHWA-D in others. The discovery of these APP mutations in genetically based cases of AD argues that genetic alteration of APP and subsequent deposition of its Aβ fragment can cause AD.

Recently, evidence has accumulated suggesting that Aβ(42) plays the key role in the process of senile plaque formation in AD. First, in vitro data demonstrate that Aβ(42) accelerates the formation of Aβ fibrils (and thus senile plaques) by a nucleation dependent mechanism (Jarrett et al. (1993) *Biochemistry* 32:4693–4697). Second, while accounting for ≦10% of total Aβ secreted from cells (roughly 90% is Aβ(40) (Dovey et al. (1993) *Neuroreport* 4:1039–1042; Asami-Odaka et al. (1995) "Long amyloid β-protein secreted from wild-type human neuroblastoma IMR-32 cells." *Biochemistry* 34:10272–10278), Aβ(42) is the major plaque component (Kang et al. (1987) *Nature* 325:733–736; Iwatsubo et al. (1994) *Neuron* 13:45–53; Iwatsubo et al. (1995) *Ann. Neurol.* 37:294–299; Gravina et al. (1995) *J. Biol. Chem.* 270:7013–7016; Lemere et al. (1996) *Neurobiology of Disease* 3:16–3.2). Furthermore, all 3 early onset familial AD genes identified to date have been shown to lead to an increase in cellular secretion of Aβ(42). Only the Swedish APP missense mutation increases the secretion of both Aβ(40) and Aβ(42) peptides (Dovey et al. (1993) *Neuroreport* 4:1039–1042, whereas the APP717 mutations and the presenilin mutations appear not to increase Aβ(40) peptides (Suzuki et al. (1994) *Science* 264:1336–1340; Scheuner et al. (1995) *Neurosci. Abstracts* in press). Thus, the longer Aβ(42) peptide appears to be a prime target for therapeutic intervention. However, none of the proteases involved in the major steps of APP processing have been definitively identified, including γ-secretase, the protease which generates the C-terminus of Aβ. It has generally been assumed that the same protease(s) generate both Aβ(40) and Aβ(42) and it has been shown that both forms share a common secretory mechanism which involves acidic intracellular compartments such as the late Golgi or early endosomes (Koo and Squazzo (1994) *J. Biol. Chem.* 269:17386–17389; Asami-Odaka et al. (1995) *Biochemistry* 34:10272–10278). Recently, Higaki et al. ((1995) *Neuron*, 14:651–659) have shown that the Calpain inhibitor, MDL 28170, inhibits the production of both total Aβ and total p3 and leads to an accumulation of their respective 12 kDa and 10 kDa APP precursor fragments in treated cells. These data suggest that the compound directly inhibits at least some form of γ-secretase although no data are provided as to what specific form of Aβ and p3 are affected.

Despite the progress which has been made in understanding the underlying mechanisms of AD, there remains a need for assays to identify candidate compounds for preventing or treating the disease.

SUMMARY OF THE INVENTION

According to current theory, the processing of APP is believed to involve several specific cleavages by proteases. The enzyme that cleaves APP between amino acids 671/672 (referring to the βAPP$_{770}$ isoform) is called β-secretase. The enzyme that cleaves between amino acids 687/688 of APP (16/17 of Aβ) is called α-secretase. Until now it was believed that cleavage of APP that yielded Aβ(40) and Aβ(42) was carried out by a single enzyme called γ-secretase. However, we have discovered that a compound can inhibit the production of Aβ(40) but not Aβ(42). In particular, we have discovered that compounds, thought to inhibit the production Aβ in general, actually inhibit production of Aβ(40) but not Aβ(42). This indicates that multiple γ-secretase mechanisms are at work which can be pharmacologically dissociated.

Because Aβ(42) is the major component of β-amyloid plaques and initiates amyloid plaque formation in AD patients, it is important to have tools to screen compounds to identify those that specifically inhibit the production of Aβ(42) and Aβ(40), either simultaneously or separately. The current invention provides such assays.

This invention provides methods for determining whether a compound alters the amount of at least one Aβ(x–≧41) peptide produced by a cell. The methods involve administering the compound to a culture comprising the cell; measuring the amount of the Aβ(x–≧41) peptide, specifically, in a sample from the culture; and determining whether the measured amount is different than the amount expected in a sample from a culture comprising the cell to which no compound has been administered. A difference between the measured amount and the expected amount indicates that the compound alters the amount of an Aβ(x–≧41) peptide produced by the cell.

In another aspect, this invention provides methods for determining whether a compound alters the amount of at least one Aβ(x–≧41) peptide produced by a cell and alters the amount of either total Aβ or at least one Aβ(x–≦40) peptide produced by the cell. The methods involve administering the compound to a culture comprising the cell; measuring the amount of the Aβ(x–≧41) peptide, specifically, in a sample from the culture; measuring the amount of total Aβ or the Aβ(x–≦40) peptide, specifically, in a sample from the culture; and determining whether the measured amounts are different than the amounts expected in a sample from a culture comprising the cell to which no compound has been administered. Differences between the measured amounts and the expected amounts indicate that the compound alters the amount of the Aβ(x–≧41) peptide by a cell and/or the amount of total Aβ or the Aβ(x–≦40) peptide by the cell.

In one embodiment, the amount of the Aβ peptides are measured by immunoassay and, in particular, sandwich immunoassay comprising capture binding substances bound to a solid phase and a labeled detection binding substance.

In sandwich assays for determining the amount of at least one Aβ(x–≧41) peptide, the capture antibody preferably is, specific for Aβ(x–≧41) peptides, e.g., raised against peptide NH$_2$-Cys-NH—CH$_2$—(CH$_2$)$_5$—CO-GLMVGGVVIA-COOH (SEQ ID NO:4). The detection binding substance in this assay can be an antibody specific for Aβ peptides whose amino-terminal amino acid is no. 1 of Aβ, or can be specific for an epitope within the junction region of Aβ. In another embodiment the capture binding substance for measuring the amount of at least one of Aβ(x–≧41) peptide is specific for an epitope within the junction region of Aβ and the detection binding substance is an antibody specific for Aβ(x–≧41).

In sandwich assays for determining the amount of at least one Aβ(x–≦40) peptide, the capture binding substance preferably is an antibody specific for Aβ(x–≦40) peptides, e.g., raised against the peptide NH$_2$-Cys-NH—CH$_2$—(CH$_2$)$_5$—CO-GLMVGGVV-COOH (SEQ ID NO:5). The labeled detection binding substance can be an antibody specific for the Aβ peptides whose amino-terminal amino acid is no. 1 of Aβ or an antibody specific for an epitope within the junction region of Aβ. In another embodiment the capture binding substance for measuring the amount of at least one of Aβ(x–≦40) peptide is specific for an epitope within the junction region of Aβ and the detection binding substance is an antibody specific for Aβ(x–≦40).

In sandwich assays for determining the amount of total Aβ, the capture binding substance preferably is an antibody specific for an epitope within the junction region of Aβ. The detection binding substance preferably is specific for Aβ peptides whose amino-terminal amino acid is no. 1 of Aβ.

In another embodiment of an immunoassay, the step of measuring the amount of the Aβ(x–≧41) peptide, total Aβ or the Aβ(x–≦40) peptide in a sample from the culture comprises: pulsing the culture with a radioactive label for protein; chasing the culture without a radioactive label; administering the compound to the cell during the chase period; contacting a sample from the culture with a binding substance specific for Aβ(x–≧41) peptides; contacting a sample from the culture with a binding substance specific for total Aβ or Aβ(x–≦40) peptide; and determining the amount of radioactive label attached to the binding substances.

In other embodiments of the methods the culture comprises primary human neurons, primary neurons from a transgenic PDAPP mouse (i.e., a transgenic mouse whose cells harbor a PDAPP construct), a 293 human kidney cell line, a human neuroglioma cell line, a human HeLa cell line, a primary endothelial cell line, a primary human fibroblast line, a primary lymphoblast line, human mixed brain cells, or a Chinese hamster ovary (CHO) cell line. In one embodiment the cell is a host cell transfected with a recombinant expression vector encoding a human APP, e.g., a Hardy mutation such as V717F or the Swedish mutant; causing the cell to overproduce Aβ(x–≧41) peptides. In another aspect, the methods further comprise the step of determining whether the compound is toxic to the cell.

In another aspect this invention provides kits for specifically detecting at least one Aβ(x–≧41) peptide and at least one Aβ(x–≦40) peptide in a sample. The kits include a binding substance specific for Aβ(x–≧41) peptides; and a binding substance specific for Aβ(x–≦40) peptides.

In another aspect this invention provides kits for specifically detecting at least one Aβ(x–≧41) peptide and either total Aβ or at least one Aβ(x–≦40) peptide in a sample in a sandwich immunoassay. The kits include at least two different binding substances for measuring the amount of Aβ(x–41) peptide; and at least two different binding substances for measuring the amount of total Aβ or Aβ(x–≦40) peptides.

In another aspect this invention provides methods for determining whether a compound alters the amount of at least one Aβ(x–≧41) peptide produced by a non-human mammal and alters the amount of either total Aβ or at least one Aβ(x–≦40) peptide produced in the non-human mammal. The methods involve measuring a first amount of the Aβ(x–≧41) peptide in a sample from a non-human animal used as a model of Alzheimer's disease; measuring a first amount of total Aβ or the Aβ(x–≦40) peptide in a sample from the non-human animal; administering the compound to the non-human animal; measuring a second amount of the Aβ(x–≧41) peptide in a sample from the non-human animal; measuring a second amount of total Aβ or the Aβ(x–≦40) peptide in a sample from the non-human animal; and comparing the first amounts with the second amounts. The comparison indicates whether the compound increases, decreases, or leaves unchanged the amount of the Aβ(x–≧41) peptide and increases, decreases, or leaves unchanged the amount of the Aβ(x–≦40) peptide. In certain embodiments the non-human animal is a rodent, in particular, a mouse. The non-human animal can harbor a copy of an expressible transgene sequence which encodes a Hardy mutation (e.g., V717F) or the Swedish mutation of human β-amyloid precursor protein (APP).

BRIEF DESCRIPTION OF THE DRAWINGS

FIGS. 10A–H. The DNA sequence (SEQ ID NO:2) and the deduced amino acid sequence (SEQ ID NO:3) of APP770.

DETAILED DESCRIPTION OF THE INVENTION

I. DEFINITIONS

Figure 1:
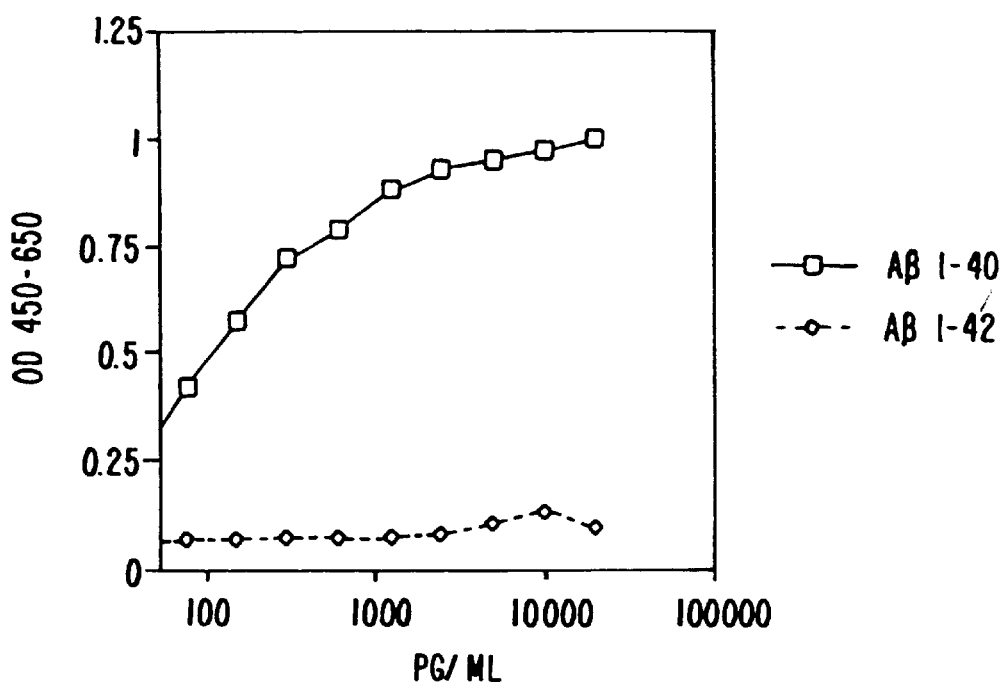
FIG. 1. Shows standard curves of Aβ(1–40) and Aβ(1–42) with 2G3 as a capture antibody.

The term "binding substance" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Antibodies exist, e.g., as intact immunoglobulins or as a number of well characterized fragments produced by digestion with various peptidases. This includes, e.g., Fab' and F(ab)'$_2$ fragments. The term "binding substance," as used herein, also includes antibody fragments either produced by the modification of whole antibodies or those synthesized de novo using recombinant DNA methodologies.

The term "immunoassay" is an assay that utilizes a binding substance to specifically bind an analyte. The immunoassay is characterized by the use of specific binding properties of a particular antibody to isolate, target, and/or quantify the analyte.

A binding substance "specifically binds to" or "is specifically immunoreactive with" a protein when the binding substance functions in a binding reaction which is determinative of the presence of the protein in the presence of a heterogeneous population of proteins and other biologics. Thus, under designated immunoassay conditions, the specified binding substances bind preferentially to a particular protein and do not bind in a significant amount to other proteins present in the sample. Specific binding to a protein under such conditions requires an antibody that is selected for its specificity for a particular protein. A variety of immunoassay formats may be used to select binding substances specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity.

A "label" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, dioxigenin, or haptens and proteins for which antisera or monoclonal antibodies are available. Binding substances can be made detectible, e.g., by incorporating a radio-label into the peptide, and used to detect antibodies specifically reactive with the peptide. A label often generates a measurable signal, such as radioactivity, fluorescent light or enzyme activity, which can be used to quantitate the amount of bound label.

II. IN VITRO SCREENING

Alzheimer's disease is characterized by the initial deposition of Aβ(x–≧41) in the form of amyloid plaques in the brain. Therefore, effective treatments for AD are expected to decrease the production of these peptides, whereas agents that hasten progress of the disease are expected to increase production of the peptide. Prior screening methods looked for compounds that decreased total Aβ. However, since Aβ(x–≧41) peptides are a small fraction of total Aβ, those assays could not determine whether the compound specifically inhibited Aβ(x–≧41) peptides. As results described herein indicate, compounds can alter the production of Aβ(x–≦40) but not Aβ(x–≧41). Because Aβ(42) is the major constituent of neuritic plaques, it is useful to identify compounds that specifically inhibit the production of Aβ(x–≧41) peptides, either in addition to, or instead of Aβ(x–≦40) peptides. Accordingly, this invention provides methods for screening compounds that specifically elevate or decrease the production of the amount of Aβ(x–≧41) by a cell and compounds that elevate or decrease production of both Aβ(x–≧41) and Aβ(x–≦40) (e.g., total Aβ), or of one or the other of these peptides. Compounds that decrease production of Aβ(x–≧41) are candidates for use in treating the disease, while compounds that increase its production may hasten the disease and are to be avoided by humans.

Screening methods of this invention for determining whether a test compound specifically alters the amount of Aβ(x–≧41) produced by a cell involve administering the compound to the cell, usually in culture, measuring the amount of Aβ(x–≧41) specifically produced by the cell, and determining whether this amount is greater than, less than or the same as an amount the cell is expected to produce in the absence of the compound. If the amounts are different, then the compound affects the production of Aβ(x–≧41) by the cell. This amount can be measured, for example, in a sample from the culture, such as medium conditioned by the cell in culture, or in extracts derived from cells harvested from the culture.

The expected amount generally will be a control amount determined by measuring Aβ(x–≧41) produced by the cell in the absence of the compound. However, one also may determine the expected amount by extrapolation; measuring the amount of Aβ(x–≧41) produced upon administration of different amounts of the compound to the cell, and using these figures to calculate the expected amount. In certain instances measuring a control amount for the purposes of comparison may not be necessary because the effect of the compound on Aβ(x–≧41) production is clear. For example, a compound may render Aβ(x–≧41) undetectable in a cell that normally produces detectable amounts, indicating that the compound decreases Aβ(x–≧41) production from the amount expected in its absence.

In another aspect, this invention provides screening methods for determining whether a compound alters the production of Aβ(x–≧41) by a cell to a different degree than it alters the production of total Aβ or Aβ(x–≦40) by the cell.

These methods are useful for determining whether a compound alters the production of Aβ(x–≧41) in addition to total Aβ, or alters the production of one or the other of Aβ(x–≧41) and Aβ(x–≦40). The methods involve administering the compound to the cell (usually in culture). Then, the degree to which the compound alters the production of Aβ(x–≧41), specifically, by the cell is determined. The degree to which the compound alters the production of total Aβ or Aβ(x–≦40) by the cell also is determined. Then, the degrees are compared. The comparison indicates whether the compound alters the production of Aβ(x–≧41) instead of or in addition to Aβ(x–≦40).

Determining the degree to which a compound alters the production of one or the other peptide generally involves measuring the specific amount of the peptide in a sample from the culture; and comparing it with the amounts expected in a sample from a culture comprising the cell to which no compound has been administered.

III. AMYLOID-β PEPTIDE AND RELATED PROTEINS AND PEPTIDES

Figure 7:
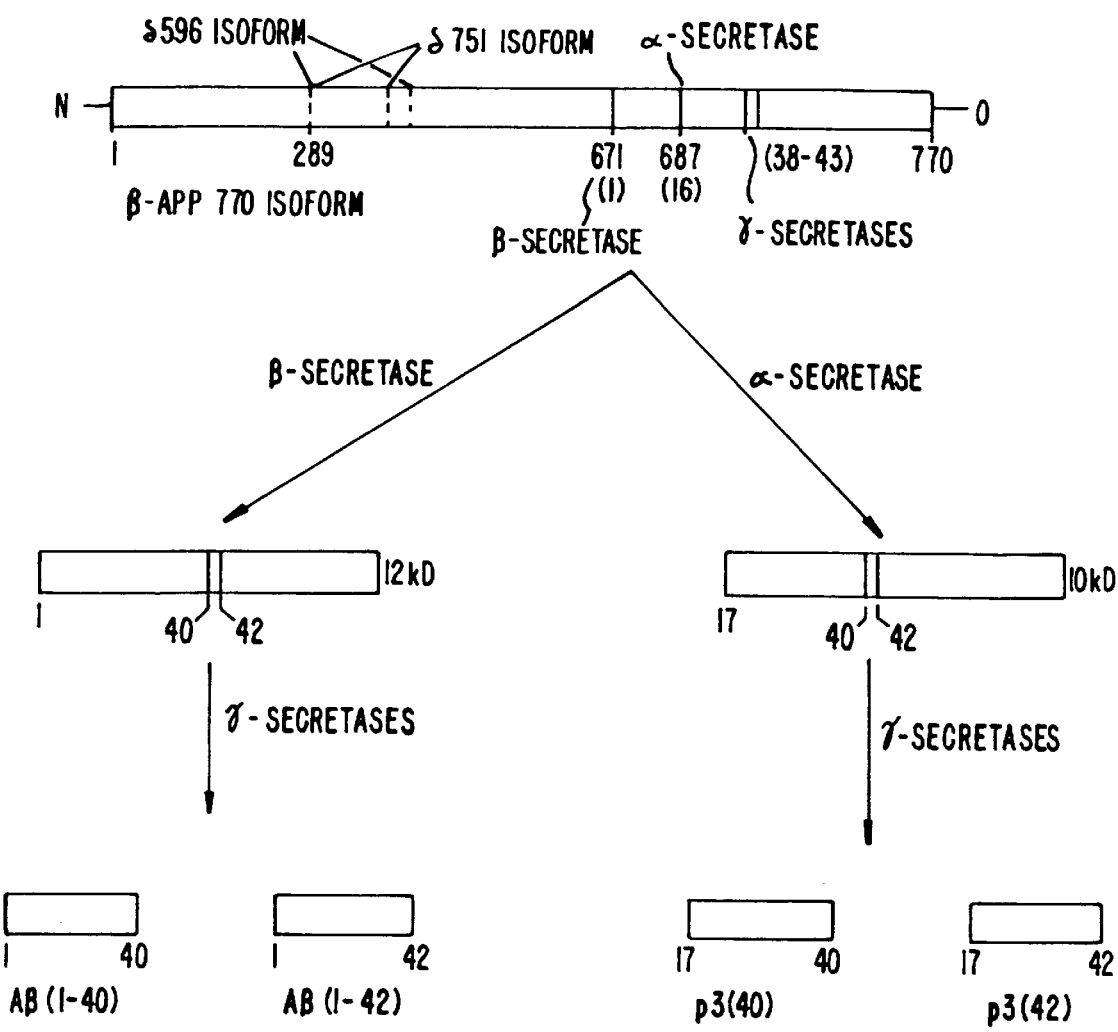
FIG. 7. Shows a summary sketch of some of the known proteolytic processing pathways of APP.

Various cellular processing pathways for APP are presented in FIG. 7. The terms "amyloid-β peptide," "Aβ" or "βAP" as used herein refer to an approximately 4.2 kD protein which, in the brains of AD, Down's Syndrome, HCHWA-D and some normal aged subjects, forms the subunit of the amyloid filaments comprising the senile (amyloid) plaques and the amyloid deposits in small cerebral and meningeal blood vessels (amyloid angiopathy). Aβ can occur in a filamentous polymeric form (in this form, it exhibits the Congo-red and thioflavin-S dye-binding characteristics of amyloid described in connection therewith). Aβ can also occur in a non-filamentous form ("preamyloid" or "amorphous" or "diffuse" deposits) in brain tissue, in which form no birefringent staining by Congo red occurs. A portion of this protein in the insoluble form obtained from meningeal blood vessels is described in U.S. Pat. No. 4,666,829.

Aβ is an approximately 39–43 amino acid fragment of a large membrane-spanning glycoprotein, referred to as the β-amyloid precursor protein (APP), encoded by a gene on the long arm of human chromosome 21. Forms of Aβ longer than 43 amino acids are also contemplated herein. Aβ is further characterized by its relative mobility in SDS-polyacrylamide gel electrophoresis or in high performance liquid chromatography (HPLC). A sequence for a 43-amino acid-version of Aβ is:

1
  Asp Ala Glu Phe Arg His Asp Ser Gly Tyr
11
  Glu Val His His Gln Lys Leu Val Phe Phe
21
  Ala Glu Asp Val Gly Ser Asn Lys Gly Ala
31
  Ile Ile Gly Leu Met Val Gly Gly Val Val
41
Ile Ala Thr (SEQ ID NO:1).

As used herein, Aβ also refers to related polymorphic forms of Aβ, including those that result from mutations in the Aβ region of the APP gene.

The term "Aβ fragment" as used herein refers to fragments and degradation products of Aβ which are generated at low concentrations by mammalian cells. Particular Aβ fragments have a molecular weight of approximately 3 kD and are presently believed to include peptides with, for example, amino acid residues 3–34, 6–27, 6–34, 6–35, 6–42, 11–34, 11–40, 11–43, 12–43, 17–40 and 17–42 of Aβ (Vigo-Pelfrey et al. (1993) *J. Neurochem.* 61:1965–1968).

As used herein, the term "Aβ(x–≧41)" refers to Aβ or an Aβ fragment whose amino-terminus begins at amino acid number 1 of Aβ or thereafter (i.e., which is amino-terminally truncated), and whose carboxy-terminus extends beyond amino acid number 40. These peptides and fragments comprise a heterogenous group. For example, Aβ(6–42), Aβ(11–43) and Aβ(12–43) all have been found in the CSF. However, this list is not meant to be exclusive. Other peptides from among the group are presumed to exist in the culture media of cells expressing APP and are detectable with the methods described herein. As used herein the term "Aβ(42)" refers to Aβ or an Aβ fragment whose C-terminal amino acid is #42 of Aβ.

As used herein, the term "Aβ(x–≦40)" refers to Aβ or an Aβ fragment whose amino-terminus begins at amino acid number 1 of Aβ or which is amino-terminally truncated, and whose carboxy-terminus extends no further than amino acid number 40. These peptides and fragments also comprise a heterogenous group. The term "Aβ(40)" refers to Aβ or an Aβ fragment whose C-terminal amino acid is #40 of Aβ.

As used herein, the term "p3" refers to a peptide whose amino acid sequence is substantially similar to Aβ, but whose amino-terminal amino acid begins at amino acid 17 of Aβ. The term "p3 fragment" as used herein refers to fragments and degradation products of p3. Whereas p3 is produced through a different processing pathway than Aβ, for the purposes of the detection methods of this invention, p3 and p3 fragments are considered to be a subset of Aβ peptides, because certain detection techniques that recognize Aβ solely from the carboxy-terminus generally also will recognize p3. Also it is shown that the same apparent mechanisms generate the p3 and Aβ carboxy-termini.

The term "Aβ junction region" as used herein refers to a region of Aβ which is centered at the site between amino acid residues 16 and 17 ($Lys^{16}$ and $Leu^{17}$), which is a principal target for proteolytic processing of APP. Such processing, referred to as "α-secretory" processing, results in a variety of APP fragments which may, for example, terminate at amino acid 16 of Aβ and which, therefore, are potentially immunologically cross-reactive with antibodies to the intact Aβ molecule which are to be used in the methods of the present invention. Antibodies raised against a synthetic peptide including amino acid residues 13–28 have been found to display the requisite specificity for the junction region.

The term "amyloid-β precursor protein" (APP) as used herein is defined as a polypeptide that is encoded by a gene of the same name localized in humans on the long arm of chromosome 21 and that includes the Aβ region within the carboxyl third of its coding region. APP is a glycosylated, single-membrane-spanning protein expressed in a wide variety of cells in many mammalian tissues. Examples of specific isotypes of APP which are currently known to exist in humans are the 695-amino acid polypeptide described by Kang et al. (1987) *Nature* 325:733–736; the 751-amino acid polypeptide described by Ponte et al. (1988) *Nature* 331:525–527 (1988) and Tanzi et al. (1988) *Nature* 331:528–530; and the 770-amino acid polypeptide described by Kitaguchi et al. (1988) *Nature* 331:530–532. Examples of specific variants of APP include point mutations which can differ in both position and resultant neuropathological phenotype (for review of known variant mutations see Hardy (1992) *Nature Genet.* 1:233–234).

The term "Aβ-related condition" as used herein is defined as including Alzheimer's disease (which includes familial Alzheimer's disease), Down's Syndrome, HCHWA-D, and advanced aging of the brain.

IV. CELLS EXPRESSING Aβ(x–≧41)

Because it is a therapeutic goal to discover compounds that inhibit the production of Aβ(x–≧41), the test cells used in the methods of this invention generally are ones that are able to secrete Aβ(x–≧41).

In vitro monitoring of Aβ(x–≧41) levels in conditioned medium from a suitable cell culture may be used for drug screening. By growing cells under conditions which result in the secretion of Aβ(x–≧41) into the culture medium, and exposing the cells to test compounds, the effect of these test compounds on Aβ(x–≧41) secretion can be observed.

Suitable cell lines include human and animal cell lines, such as, preferably, primary human neurons, and primary neurons from transgenic mice harboring human APP genes, e.g., cells from a transgenic PDAPP animal (e.g., mouse), as well as a 293 human kidney cell line, a human neuroglioma cell line, a human HeLa cell line, a primary endothelial cell line (e.g., HUVEC cells), a primary human fibroblast line or a primary lymphoblast line (including endogenous cells derived from patients with APP mutations), a primary human mixed brain cell culture (including neurons, astrocytes and neuroglia), or a Chinese hamster ovary (CHO) cell line. Particularly useful are cells stably transfected with $APP_{695}$ carrying the mutation V717I (valine to isoleucine at position 717 in the APP770 numbering system). Cell lines which preferentially increase the levels or ratios of Aβ(x–≧41) would be particularly useful in the methods of invention. Useful mutants at position 717 (the Hardy mutation) include V717F,. V717I or V717G.

Preferred for use in drug screening methods according to the present invention are cell lines capable of expressing APP variants which overproduce Aβ. By "overproduce," it is meant that the amount of Aβ produced from the variant APP will be at least about one-and-a-half times and preferably at least two or five times greater than the amount produced from any or all of the normal APP isoforms, e.g., the 695, 751, and 770 amino acid isoforms which have been previously described. Particularly preferred are APP variants having one or several amino acid substitutions directly amino-terminal of the Aβ cleavage site. For example, K293 cells which express an $APP_{695}$ DNA bearing a double mutation ($Lys^{595}$->$Asn^{595}$ and $Met^{596}$->$Leu^{596}$ (695 numbering system)) found in a Swedish FAD family produce approximately five-to-eight-fold more Aβ than cells expressing normal APP (Citron et al. (1992) *Nature*, 360:672–674). The mutation at residue 596 appears to be principally responsible for the increase.

V. EXPRESSION VECTORS FOR APP

Host cells transfected with a recombinant expression vector that encodes APP also are useful as cells in the screening methods of this invention. A plasmid that carries sequences encoding APP is pCMV695 (Selkoe et al. (1988) *Proc. Natl. Acad. Sci USA* 85:7341–7345).

Nucleic acids encoding APP can be obtained by methods known in the art. For example, a nucleic acid encoding an APP can be isolated by polymerase chain reaction of cDNA or genomic DNA from a human brain cDNA library or a human genomic library using primers based on the DNA sequence of APP. PCR methods are described in, for example, U.S. Pat. No. 4,683,195; Mullis et al. (1987) *Cold Spring Harbor Symp. Quant. Biol.* 51:263; and Erlich, ed., *PCR Technology*, (Stockton Press, NY, 1989).

Mutant versions of APP, such as the Swedish mutation, can be made by site-specific mutagenesis of other nucleic acids encoding APP, or by random mutagenesis caused by increasing the error rate of PCR of the original polynucleotide with 0.1 mM $MnCl_2$ and unbalanced nucleotide concentrations.

The construction of expression vectors and the expression of genes in transfected cells involves the use of molecular cloning techniques also well known in the art. Sambrook et al., *Molecular Cloning—A Laboratory Manual*, Cold Spring Harbor Laboratory, Cold Spring Harbor, N.Y., (1989) and *Current Protocols in Molecular Biology*, F. M. Ausubel et al., eds., (Current Protocols, a joint venture between Greene Publishing Associates, Inc. and John Wiley & Sons, Inc.).

Nucleic acids used to transfect cells with sequences coding for expression of the polypeptide of interest generally will be in the form of an expression vector that includes expression control sequences operatively linked to a nucleotide sequence coding for expression of the polypeptide. As used herein, the term nucleotide sequence "coding for expression of" a polypeptide refers to a sequence that, upon transcription and translation of mRNA, produces the polypeptide. As any person skilled in the art recognizes, this includes all degenerate nucleic acid sequences encoding the same amino acid sequence. This can include sequences containing, e.g., introns. As used herein, the term "expression control sequences" refers to nucleic acid sequences that regulate the expression of a nucleic acid sequence to which it is operatively linked. Expression control sequences are "operatively linked" to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

The recombinant nucleic acid can be incorporated into an expression vector comprising expression control sequences operatively linked to the recombinant nucleic acid. The expression vector can be adapted for function in prokaryotes or eukaryotes by inclusion of appropriate promoters, replication sequences, markers, etc.

The expression vector can be transfected into a host cell for expression of the recombinant nucleic acid. Host cells can be selected for high levels of expression in order to purify the protein. The host cell can be a prokaryotic or eukaryotic cell selected to study the activity of an enzyme produced by the cell. The cell can be, e.g., a cultured cell or a cell in vivo.

Transfected host cells useful in this invention include human kidney 293 cell lines such as K695sw, and $K695^{717I}$, glioma cell lines such as HS695, and neuroblastoma cell lines such as SKN695, described in the Experimental section.

VI. MEASURING Aβ(x–≧41)

Aβ peptides can be detected by any method known in the art. Preferably, the method involves an immunoassay employing binding substances specific for the peptides. Optionally, one can detect Aβ peptides by determining their size, e.g., by HPLC or by mass spectrometry.

A. Binding Substances

One step of the screening methods of this invention involves measuring the amount of at least one Aβ(x–≧41)

peptide, specifically, in a sample. Measuring Aβ(x–≧41) peptides specifically means measuring Aβ(x–≧41) peptides so as to distinguish that molecule from shorter species of Aβ, i.e., those species whose carboxy-terminus extends no further than amino acid #40 of Aβ.

Specific measurement of Aβ(x–≧41) preferably is performed by the use of binding substances that specifically recognize Aβ(x–≧41) peptides, e.g., binding substances that recognize amino acids of Aβ beyond amino acid #40.

Another method of this invention involves screening compounds to determine their ability to alter the production of both Aβ(x–≧41) peptides and total Aβ or Aβ(x–≦40) peptides. Such methods can involve the use of binding substances that can distinguish Aβ(x–≦40) peptides from longer species of Aβ, such as Aβ(x–≧41) peptides.

B. Immunoassays

The use of immunological detection techniques, i.e., immunoassays employing binding substances, is preferred. Particularly suitable detection techniques include ELISA, Western blotting, radioimmunoassay, and the like. Suitable immunological methods employing a single antibody are also contemplated, for example, radioimmunoassay using an antibody specific for ≧41 forms of Aβ, or single antibody ELISA methods. It will be clear that the particular forms of Aβ detected by such methods depend upon the particular binding substances employed. For example, binding substances directed to the junction region may detect Aβ(x–≧41) peptides whose amino termini do not extend to amino acid no. 1 of Aβ. Also, binding substances directed to the carboxy-terminal end of Aβ(x–≧41) may detect peptides ending at amino acids 41, 42 or 43. Therefore, determining the specificity of the binding substances will assist in determining exactly which Aβ(x–≧41) peptides the assay is detecting.

In one embodiment, the method to detect Aβ(x–≧41) peptides is an immunoassay involving two antibodies. One antibody is specific for an epitope containing amino acids beyond number 40 in Aβ, and another antibody is capable of distinguishing Aβ and Aβ fragments from other APP fragments which might be found in the sample. In particular, it has been found that antibodies which are monospecific for the junction region of Aβ are capable of distinguishing Aβ from other APP fragments. The junction region of Aβ is centered at amino acid residues 16 and 17, typically spanning amino acid residues 13 to 28. Such "junction-recognizing" antibodies may be prepared using synthetic peptides having that sequence as an immunogen.

A preferred immunoassay technique is a two-site or "sandwich" assay. This assay involves a capture binding substance, usually bound to a solid phase, and a labelled detection binding substance. In this method, Aβ(x–≧41) peptides are captured from the sample using a first binding substance specific for Aβ(x–≧41) peptides (usually bound to a solid phase). The capture of Aβ(x–≧41) peptides is detected using a labeled second binding substance specific for Aβ. Labeled binding substances include, for example, those directed to the junction region (amino acids 13 to 28) or binding substances specific for amino-terminal amino acids (1–5 or 1–12).

Particular methods for preparing such antibodies and utilizing such antibodies in an exemplary ELISA are set forth in the Experimental section hereinafter and in related U.S. patent application Ser. No. 07/965,972, supra. A sandwich assay using an antibody against the junction region can be used to specifically measure Aβ and Aβ fragments whose amino-terminus begins before amino acid 13 of Aβ. Such assays do not recognize p3 or p3 fragments, since those peptides begin at amino acid #17 of Aβ.

Antibodies specific for Aβ(x–≧41), i.e., which do not cross react with Aβ(≦40), are particularly useful in the methods of this invention. These antibodies can be made by immunizing animals with synthetic peptides that include amino acids beyond number 40 of Aβ. For example, the synthetic peptide can include amino acids 33–42. A specific example of the production of such an antibody is provided in the Experimental section.

The particular peptides measured from among the group of all Aβ(x–≧41) depends on the particular measuring method used. In the case of using binding substances, such as antibodies, the binding substance can be directed to one or more from among the group of peptides. For example, an antibody raised against amino acids 33–42 of Aβ that does not cross react with Aβ(1–40) will bind to Aβ(x–42). It also may bind to Aβ(x–41) and Aβ(x–3). According to one embodiment of the invention, the method involves determining the amount of Aβ(x–≧41) having at least amino acids 13–41 of Aβ. These species can be measured using a sandwich assay employing antibodies that recognize the junction region (amino acids 13–26) and antibodies produced by immunization with a hapten having Aβ amino acids 33–42. Total Aβ can be measured using a capture antibody to the junction region (e.g., the 266 antibody, described herein) and a reporter antibody that should detect virtually all the Aβ peptides and Aβ fragments, e.g., an antibody raised against amino acids 1–12 of Aβ.

C. Pulse-chase Assays

Another method of measuring the amount of Aβ(x–≧41) in a sample involves pulse-chase procedures. In these methods, the culture is pulsed with a radioactive label for protein, e.g., a radioactive amino acid such as $^{35}S$ methionine. Then the culture is chased without the label. Then the compound is administered to the cells. Then the cells are contacted with a binding substance specific for Aβ(x–≧41) and the amount of radioactive label attached to the binding substance is determined.

D. Preparation of Antibodies

Antibodies specific for Aβ can be prepared, e.g., by immunizing an animal with a peptide whose amino acid sequence corresponds with amino acids ~13 to ~28 of Aβ. Antibodies specific for Aβ(x–≧41) can be prepared, e.g., by immunizing an animal with a peptide whose amino acid sequence corresponds with amino acids 33–42 of Aβ. Antibodies specific for Aβ(x–≦40) can be prepared, e.g., by immunizing an animal with a peptide whose amino acid sequence corresponds with amino acids 33–40 or 28–40 of Aβ. Antibodies against the junction region are useful for detecting total Aβ.

Synthetic polypeptide haptens may be produced by the well-known Merrifield solid-phase synthesis technique in which amino acids are sequentially added to a growing chain (Merrifield (1963) *J. Am. Chem. Soc.* 85:2149–2156). Suitable peptide haptens will usually comprise at least five contiguous residues within Aβ and may include more than six residues. The amino acid sequences may be based on the sequence of Aβ set forth above.

Once a sufficient quantity of polypeptide hapten has been obtained, it may be conjugated to a suitable immunogenic carrier, such as serum albumin, keyhole limpet hemocyanin, or other suitable protein carriers, as generally described in Hudson and Hay, *Practical Immunology*, Blackwell Scientific Publications, Oxford, Chapter 1.3, 1980. An exemplary immunogenic carrier utilized in the examples provided below is α-CD3ε antibody (Boehringer-Mannheim, Clone No. 145-2C11).

Antibodies specific for the desired epitope may be produced by in vitro or in vivo techniques. In vitro techniques involve exposure of lymphocytes to the immunogens, while in vivo techniques require the injection of the immunogens into a suitable vertebrate host. Suitable vertebrate hosts are non-human, including mice, rats, rabbits, sheep, goats, and the like. Immunogens are injected into the animal according to a predetermined schedule, and the animals are periodically bled, with successive bleeds having improved titer and specificity. The injections may be made intramuscularly, intraperitoneally, subcutaneously, or the like, and an adjuvant, such as incomplete Freund's adjuvant, may be employed.

If desired, monoclonal antibodies can be obtained by preparing immortalized cell lines capable of producing antibodies having desired specificity. Such immortalized cell lines may be produced in a variety of ways. Conveniently, a small vertebrate, such as a mouse, is hyperimmunized with the desired immunogen by the method just described. The vertebrate is then killed, usually several days after the final immunization, the spleen cells removed, and the spleen cells immortalized. The manner of immortalization is not critical. Presently, the most common technique is fusion with a myeloma cell fusion partner, as first described by Kohler and Milstein (1975) *Nature* 256:495–497. Other techniques including EBV transformation, transformation with bare DNA, e.g., oncogenes, retroviruses, etc., or any other method which provides for stable maintenance of the cell line and production of monoclonal antibodies. Specific techniques for preparing monoclonal antibodies are described in Antibodies: A Laboratory Manual, Harlow and Lane, eds., Cold Spring Harbor Laboratory, 1988.

In addition to monoclonal antibodies and polyclonal antibodies (antisera), the detection techniques of the present invention will also be able to use antibody fragments, such as F(ab), Fv, $V_L$, $V_H$, and other fragments. In the use of polyclonal antibodies, however, it may be necessary to adsorb the anti-sera against the target epitopes in order to produce a monospecific antibody population. It will also be possible to employ recombinantly produced antibodies (immunoglobulins) and variations thereof as now well described in the patent and scientific literature. See, for example, EPO 8430268.0; EPO 85102665.8; EPO 85305604.2; PCT/GB 85/00392; EPO 85115311.4; PCT/US86/002269; and Japanese application 85239543, the disclosures of which are incorporated herein by reference. It would also be possible to prepare other recombinant proteins which would mimic the binding specificity of antibodies prepared as just described.

VII. KITS

This invention also provides kits for performing assays of the invention. The kits include means for detecting specifically $A\beta(x-\geq 41)$ and means for detecting specifically $A\beta(x-\leq 40)$. The means can include any means known or described above, e.g., binding substances.

In one embodiment, the kit includes a binding substance specific for $A\beta(x-\geq 41)$ (i.e., that does not cross react with $A\beta(\leq 40)$), and a binding substance specific for $A\beta(\leq 40)$ (i.e., that does not cross react with $A\beta(x-\geq 41)$). Such kits are useful, e.g., in pulse-chase assays.

In another embodiment, the kit is useful for immunoassays including two antibodies for each antigen. For example, the kit can further comprise a binding substance specific for the junction region of Aβ. Such antibodies are useful for the capture or detection of both $A\beta(x-\geq 41)$ and $A\beta(\leq 40)$. In one kit useful for a sandwich ELISA, the binding substance specific for the junction region is bound to a solid phase, and the binding substances specific for $A\beta(x-\geq 41)$ and $A\beta(\leq 40)$ are detectably labeled.

The detectable labels can be any known and used in the art including, e.g., a biotinylation label, a radioactive label, a light scattering label, an enzymatic label, a fluorescent label and the like. When the label is enzymatic, the kit can further comprise a substrate for the enzyme.

VIII. TEST COMPOUNDS

The test compounds can be any molecule, compound, or other substance which can be added to the cell culture or administered to the test animal without substantially interfering with cell or animal viability. Suitable test compounds may be small molecules (i.e., molecules whose molecular mass is no more than 1000 Daltons), biological polymers, such as polypeptides, polysaccharides, polynucleotides, and the like. The test compounds will typically be administered to the culture medium at a concentration in the range from about 1 nM to 1 mM, usually from about 10 µM to 1 mM. The test compounds will typically be administered at a dosage of from 1 ng/kg to 100 mg/kg, usually from 10 pg/kg to 1 mg/kg.

Test compounds which are able to inhibit secretion or production of $A\beta(x-\geq 41)$ are considered as candidates for further determinations of the ability to block β-amyloid production in animals and humans. Such compounds can be tested in in vivo studies, as described below. Inhibition of secretion or production indicates that cleavage of Aβ between amino acids 42/43 has likely been at least partly blocked, reducing the amount of $A\beta(x-\geq 41)$ available for forming amyloid plaques.

IX. IN VIVO SCREENING

Animal models currently are being used to study Alzheimer's disease. (See, e.g., International Patent Application WO 93/14200, U.S. patent application Ser. No. 08/143,697, filed Oct. 27, 1993, U.S. Pat. No. 5,387,742, and U.S. application Ser. No. 08/486,538, filed Jun. 7, 1995.) These models are useful for screening compounds that alter the production of $A\beta(x-\geq 41)$ in the assays of this invention for their ability to affect the course of Alzheimer's disease, both to ameliorate and aggravate the condition. Transgenic mammalian models, more particularly, rodent models and in particular murine, hamster and guinea pig models, are suitable for this use.

A preferred non-human transgenic animal is one whose cells harbor a PDAPP construct. A PDAPP construct is a nucleic acid construct that comprises a mammalian promoter operatively linked to a cDNA-genomic DNA hybrid coding for the expression of APP. The cDNA-genomic DNA hybrid contains a cDNA sequence encoding APP770 or a cDNA sequence encoding APP770 with a naturally occurring mutation (e.g., a Hardy mutation or the Swedish mutation) substituted with genomic DNA sequences. The genomic DNA sequences consist of exon 6 and an amount of the adjacent downstream intron sufficient for splicing, the KI and OX-2 coding region and an amount of each of their upstream and downstream introns sufficient for splicing, and exon 9 and an amount of the adjacent upstream intron sufficient for splicing, substituted into the corresponding region of the cDNA sequence encoding APP770, or the cDNA encoding APP770 with a naturally occurring mutation. The construct is transcribed and differentially spliced in mammalian cells to form mRNA molecules that encode and that are translated into APP695, APP751 and APP770. In certain embodiments, the construct contains a PDGF-β promoter operatively linked with a hybrid sequence encoding an APP gene harboring a Hardy mutation (V717F), and the SV40 polyadenylation signal. One version of the PDAPP construct is presented in Example IX.

Another useful non-human animal model harbors a copy of an expressible transgene sequence which encodes the Swedish mutation of APP (asparagine$^{595}$-leucine$^{596}$). The sequence generally is expressed in cells which normally express the naturally-occurring endogenous APP gene (if present). Such transgenes typically comprise a Swedish mutation APP expression cassette, in which a linked promoter and, preferably, an enhancer drive expression of structural sequences encoding a heterologous APP polypeptide comprising the Swedish mutation. Aβ levels can be measured in any body fluid or tissue sample, for example, brain homogenate.

The transgenic animals that are usually produced by introducing the transgene or targeting construct into a fertilized egg or embryonic stem (ES) cell, typically by microinjection, electroporation, lipofection, or biolistics.

The transgenic animals express the Swedish mutation APP gene of the transgene (or homologously recombined targeting construct), typically in brain tissue. Preferably, one or both endogenous APP alleles is inactivated and incapable of expressing the wild-type APP.

In all cases, it will be necessary to obtain a control value which is characteristic of the level of Aβ(x-$\geq$41) and/or total Aβ or Aβ(x-$\leq$40) production in the test animal in the absence of test compound(s). In cases where the animal is sacrificed, it will be necessary to base the value on an average or a typical value from other test animals which have been transgenically modified to express the Swedish mutant of human APP but which have not received the administration of any test compounds or any other substances expected to affect the level of production of Aβ(x-$\geq$41) and/or total Aβ or Aβ(x-$\leq$40). Once such control level is determined, test compounds can be administered to additional test animals, in which deviation from the average control value would indicate that the test compound had an effect on the γ-secretase activity in the animal. Test substances which are considered positive, i.e., likely to be beneficial in the treatment of Alzheimer's disease or other β-amyloid-related conditions, will be those which are able to reduce the level of Aβ(x-$\geq$41) production, preferably by at least 20%, more preferably by at least 50%, and most preferably by at least 80%.

The following examples are offered by way of illustration, not by way of limitation.

EXPERIMENTAL

I. ANTIBODY PREPARATION

A. Monoclonal Antibodies to the Aβ Junction Region

Monoclonal antibodies to the junction region of Aβ were prepared using a synthetic peptide spanning amino acid residues 13–30, except that AI, amino acids 30 and 31, were substituted with GC (the "junction peptide"). The junction peptide was conjugated to an immunogen (α-CD3ϵ antibody; Clone No. 145-2C11, Boehringer-Mannheim) using m-maleimidobenzoyl-N-hydroxysuccinimide ester (MHS) according to the manufacturer's (Pierce) instructions.

A/J mice were immunized initially intraperitoneally (IP) with the Aβ conjugate mixed with complete Freund's adjuvant. Fourteen days later, the mice were boosted IP with the Aβ conjugate mixed with phosphate buffered saline (PBS) at 14 day intervals. After six total boosts, the mice were finally boosted intravenously with Aβ conjugate mixed with incomplete Freund's adjuvant and fused 3 days later. Fusion of spleen cells with P3.653 myeloma cells was performed as described in Oi and Herzenberg, *Selective Methods in Cellular Immunology*, Mishell and Shigii, Eds., W. H. Freeman and Company, San Francisco, Chapter 17 (1980). Serum titers and initial screens were performed by the RIA method described below. Several clones were expanded to a 24-well plate and subjected to further analysis as described below. Clones of interest were produced in mouse ascites.

The RIA method used to screen serum bleeds and fusion hybridoma supernatants was based upon a method developed by Wang et al. (1977) *J. Immunol. Methods* 18:157–164. Briefly, the supernatant (or serum) was incubated overnight at room temperature on a rotator with $^{125}$I-labeled Aβ$_{1-28}$ and Sepharose® 4B beads to which sheep anti-mouse IgG had been coupled via cyanogen bromide. The beads from each well were harvested onto glass fiber filter discs with a cell harvester and washed several times with PBS. The filter discs were then transferred to gamma tubes and the bound radioactivity was counted in a gamma counter.

All hybridomas were tested for binding to Aβ$_{1-28}$ using the method described above in the initial screen, and then retested 3 days later. Aβ$_{1-28}$ positive clones were further characterized for reactivity to $^{125}$I-labeled Aβ$_{1-16}$ using the RIA method described above. No clones were found to bind Aβ$_{1-16}$. In a peptide capture ELISA, all clones were found to react with Aβ$_{13-28}$ while no clones reacted with Aβ$_{17-28}$. Therefore, it was determined that all clones had an epitope within the junction region spanning amino acids 16 and 17.

Based on results of the above assays, several clones were expanded into 24 well plates. These clones were further characterized by saturation analysis. Supernatants at the 50% titer point (as determined by the RIA method described above) were added to wells containing Sepharose®-sheep anti-mouse IgG beads, a constant amount of $^{125}$I-labeled Aβ$_{1-28}$, and varying amounts of unlabeled junction peptide or Aβ$_{17-28}$. The concentration of cold peptide for 50% inhibition was determined for each antibody. For the Aβ$_{17-28}$, no inhibition was seen at 100 ng/well for any clones. The 50% inhibition point for junction peptide ranged from 10–80 ng/well. The clones were also characterized based on reactivity in Western blots. Based on titer point, sensitivity (as determined by the 50% inhibition point), and reactivity on Western blot, several clones were produced in ascites. Antibodies from hybridoma designated 266 (the "266 antibody") was selected for use as a capture antibody in the assays described below.

Supernatants from wells containing hybridoma cells were screened for antibody with the ability to capture $^{125}$I labeled Aβ 1–42 in solution by immunoprecipitation (Notebook 1101).

B. 2G3 Production

Antibody 2G3, specific for Aβ(x–40), was produced by injecting female A/J mice intraperitoneally with 100 μg immunogen per injection. The immunogen consisted of the peptide NH$_2$-Cys-NH—CH$_2$—(CH$_2$)$_5$—CO-GLMVGGVV-COOH (SEQ ID NO:5), coupled to sheep anti-mouse IgG using maleimidohexanoyl-N-hydroxysuccinimide. The immunogen was emulsified with Freund's complete adjuvant for the first immunization, and all subsequent immunizations were with 100 μg of immunogen emulsified with Freund's incomplete adjuvant at approximately two week intervals.

Three days before fusion, a mouse was boosted with PBS solutions containing 50 μg immunogen intravenously and 50 μg intraperitoneally in PBS. The mouse was sacrificed, the spleen was removed, splenocytes were isolated and fused with the SP2/0 mouse myeloma using a modification of the method of Koehler and Milstein.

Supernatants from wells containing hybridoma cells were screened for the ability to produce antibody which recognizes Aβ(1–40) which had been coated onto an ELISA plate. "Positives" were further screened for their ability to capture $^{125}$I Aβ(1–40) in solution by immunoprecipitation.

C. Production of 21F12

Antibody 21F12, specific for Aβ(x≧41) was produced by immunizing A/J mice intraperitoneally with 100 μg of immunogen per injection. The immunogen consists of the synthetic peptide $NH_2$-Cys-NH—$CH_2(CH_2)_5$—CO-GLMVGGVVIA-COOH (SEQ ID NO:4) coupled to sheep anti-mouse IgG using maleimidohexanoyl-N-hydroxysuccinimide (MHS). The immunogen was emulsified with Freund's complete adjuvant for the first immunization, and all subsequent immunizations were with 100 μg of immunogen emulsified with Freund's incomplete adjuvant at approximately two week intervals.

Three days before the fusion, a mouse was injected with 50 μg of immunogen each intravenously and intraperitoneally of immunogen in PBS. Three days post injection, the spleen was removed, splenocytes were isolated and fused with SP2/0 following a modification of the method of Koehler and Milstein.

D. Specificity of 2G3 and 21F12

Figure 2:
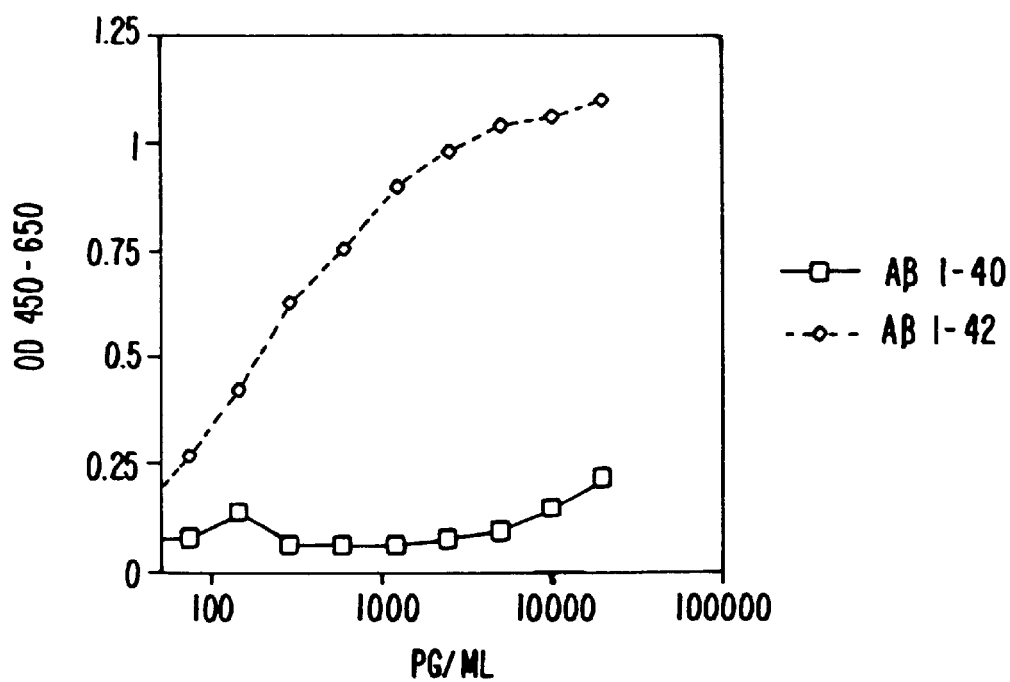
FIG. 2. Shows standard curves of Aβ(1–40) and Aβ(1–42) with 21F12 as a capture antibody.

The specificities of antibody 2G3 and 21F12 are demonstrated in FIGS. 1 and 2. In this assay, antibody 2G3 or 21F12 was coated into the wells of an ELISA plate by diluting the purified antibody to a concentration of 10 μg/ml in Well-coating Buffer (0.01 M $PO_4$ pH 8.5), and pipetting 100 μl of the antibody solution into each well. The solution was left overnight at room temperature and then was removed by aspiration. The non-specific sites of the well were blocked by the addition of 200 μl 0.25% Human Serum albumin in PBS and incubated for at least one hour at room temperature. The blocking solution was removed and the wells were washed one time with wash buffer (Tris buffered Saline, 0.05% Tween 20).

Standards containing between 80–20,000 pg/ml of either Aβ(1–40) or Aβ(1–42) were then prepared by dilution in Specimen Diluent (1 mM $PO_4$, 0.15 M NaCl, pH 7.4, 0.6% Bovine Serum albumin, globulin-free, 0.05% Triton X-405 and 0.05% Thimerosal), and 100 μl of each of these standards were added to the appropriate wells. The standards were incubated for one hour at room temperature, then aspirated and the wells washed four times with wash buffer.

100 μl of a second antibody (the reporter antibody) was added at a concentration of 0.5 μg/ml in specimen diluent. This reporter antibody is biotinylated 3D6 (which recognizes Aβ(1–5)) prepared by the reaction of antibody with NHS-biotin (Pierce). This was allowed to incubate one hour at room temperature, and then washed four times with wash buffer.

To each well, 100 μl of a 1/5000 dilution of avidin HRP (Vector Labs) was added and allowed to incubate one hour at room temperature. The wells were washed four times in wash buffer, and 100 μl of Slow TMB (Pierce) were added to each well and incubated fifteen minutes. The reaction was stopped by the addition of 25 μl of 2 M $H_2SO_4$ and the plates were read at 450–650 on a Vmax reader (Molecular Devices) (Notebook 1344).

As can be seen in FIG. 1, antibody 2G3 reacts strongly with Aβ(1–40), but has essentially no cross-reactivity with Aβ(1–42). In FIG. 2, it is shown that antibody 21F12 similarly has very high specificity, in this case for Aβ(1–42) over Aβ(1–40). At a concentration of 20,000 pg/ml less than 0.4% of cross reactivity is observed.

II. ELISA ASSAY

A. Binding of Capture Antibody to Microtiter Wells

A monoclonal antibody against Aβ(x≧41) or Aβ(x≦40) is diluted to a concentration of 10 μg/ml in a buffer containing 0.23 g/L $NaH_2PO_4.H_2O$, 26.2 g/L $Na_2HPO_4.7H_2O$, 1 g/L $NaN_3$, pH 8.5. One hundred μl/well of this solution is then dispensed in a 96 well white Dynatech Microlite 2, 96 well flat-bottomed plate. The plates are sealed and incubated overnight at room temperature. Following coating, the remaining solution is aspirated and the non-specific binding sites are blocked with 200 μL per well of ($NaH_2PO_4.H_2O$) 0.2 g/L, $Na_2HPO_4.7H_2O$ 0.8 g/L, human serum albumin (HSA) crystallized and lyophilized 2.5 g/L, pH 7.4. These plates are blocked by incubating for 1 hour at room temperature in the blocking solution.

B. Assay Protocol

The calibrators are prepared from a stock solution of Aβ$_{1-42}$, 1 μg/ml, in DMSO. In specimen diluent (($NaH_2PO_4.H_2O$) 0.2 g/L, $Na_2HPO_4.7H_2O$ 2.16 g/L, $NaN_3$ 0.5 g/L, bovine serum albumin (BSA) (globulin free) 6 g/L, triton x-405 0.5 ml/L NaCl 8.5 g/L, pH 7.4.), the highest calibrator, 1000 pg/ml (10 μl Aβ$_{1-42}$ stock (1 g/ml DMSO) in 10 ml casein specimen diluent) is prepared. Sequential dilutions are made in specimen diluent to obtain 500, 250, 125, 62.5 and 31.25 pg/ml concentrations of Aβ$_{1-42}$.

One hundred μL per well calibrators or samples are applied to the microtiter plates. The plates are sealed and incubated for 1 hour at room temperature. The plates are then washed three times with washing buffer (NaCl 80 g/L, KCl 3.85 g/L, Tris-HCl 31.75 g/L, tween-20 0.5 ml/L, pH 7.5).

Antibody is diluted in specimen diluent to 1 g/ml and 100 μl is added per well. The plate is covered and incubated for 1 hour at room temperature. The plate is washed three times with washing buffer. The alkaline phosphatase affinity purified F(ab')2 fragment donkey anti-rabbit IgG (H+L) (Jackson) is diluted 1:1000 in specimen diluent. One hundred μl/well is added. The plate is covered and incubated for 1 hour at room temperature. The plate is washed three times with washing buffer, then 100 μl/well of chemiluminescent substrate is added. The chemiluminescent substrate is prepared by diluting the chemiluminescent reagent, AMPPD (Tropix), and an enhancer, emerald green (Tropix), 1:1000 and 1:100 respectively in 1M diethanolemine buffer, pH 10, containing 1 mM $MgCl_2$ and 0.2% $NaN_3$. The plates are sealed and incubated for 10 to 15 minutes at room temperature. Solution is not aspirated. This time may have to be optimized for different antibody lots.

Chemiluminescence is read and expressed as relative chemiluminescence units (CLU) after 15 minutes using a Dynatech ML 1000.

III. INHIBITION OF APP PROCESSING BY THE MDL 28170 INHIBITOR

We first set out to reproduce the published results of Higaki et al. (1995) *Neuron*, 14:651–659 on the action of the compound MDL 28170 on APP processing, using human kidney 293 cells stably expressing APP$_{695}$ with the Swedish FAD mutation (K695sw cells). Our experiments were done using a pulse-chase paradigm: K695sw cells were labeled for 2 hours with 35S-methionine and then chased for 2 hours in the presence of 200 μM MDL 28170. Aliquots of the chase media from treated and untreated cells were subjected to SDS-PAGE. No significant differences in the amounts of the major secreted cellular proteins were detected (FIG. 3, lanes 1, 2), suggesting that under the conditions of the experiment, MDL 28170 does not interfere with general protein secretion.

We next analyzed the chase media for changes in the amounts of α- and β-cleaved APP$_s$, using antibodies specific for each form. Antibody 1736 specifically immunoprecipitates α-cleaved APP$_s$ (Haass et al. (1994) *J. Biol. Chem.* 269:17741–17748; Haass et al. (1995) *Nature Med.* 1:1291–1296). This antibody revealed an increase in α-APP$_s$ production upon treatment (FIG. 3, lanes 3, 4), indicating that MDL 28170 does not significantly inhibit α-secretase.

Figure 3:
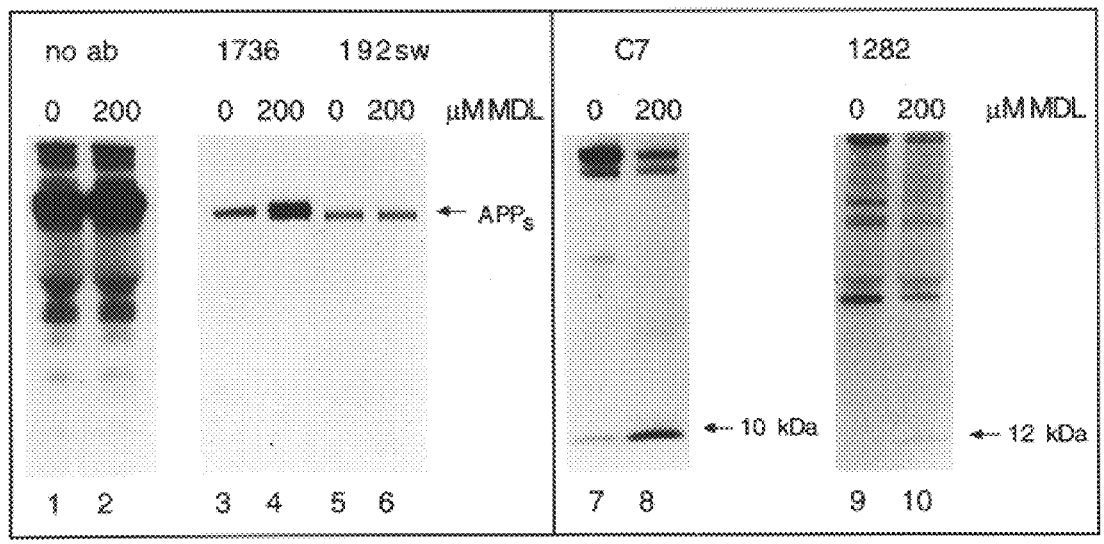
FIG. 3. Shows that compound MDL 28170 influences βAPP metabolism. (0) untreated K695sw cells; (200) K695sw cells treated with 200 μM MDL 28170 during the chase period. Lanes 1,2: aliquot of total chase media run directly on the gel. Lanes 3,4: antibody 1736 immunoprecipitation of chase media. Lanes 5,6: antibody 192sw immunoprecipitation of chase media. Note that β-cut APPs (lanes 5,6) runs slightly below α-cut APPs (lanes 3,4), as expected. Lanes 7,8: antibody C7 immunoprecipitation of cell lysates. Lanes 9,10: antibody 1282 immunoprecipitation of cell lysates.

192sw specifically immunoprecipitates the β-cleaved APP$_s$ species ending with the Swedish mutant met$_{596}$ (Knops et al. (1995) *J. Biol. Chem.* 270:2419–2422; Haass et al.(1995) *Nature Med.* 1:1291–1296). Immunoprecipitation with this antibody showed that MDL 28170 does not significantly inhibit β-secretase activity (FIG. 3, lanes 5, 6).

We next analyzed lysates of the K695sw cells for changes in cellular full-length APP and its C-terminal fragments using antibody C7, directed to the last 20 amino acids of APP (Podlisny et al. (1991) *Am. J. Pathol.* 138:1423–1435). This antibody precipitates N'- and N'/O'-glycosylated full-length APP and its 10 kDa C-terminal fragment (residues 613–695 of APP$_{695}$) that remains membrane bound after α-secretase cleavage. Upon treatment with MDL 28170, a striking increase in the level of the 10 kDa C-terminal fragment was observed (FIG. 3, lanes 7, 8).

In K695sw cells, the 12 kDa C-terminal fragment (residues 597–695 of APP$_{695}$) which remains membrane bound after β-secretase cleavage cannot be easily resolved and detected by antibody C7 (Citron et al., 1995). We therefore precipitated this fragment using antibody 1282 raised to synthetic Aβ(1–40). This antibody can precipitate the 12 kDa C-terminal but not the 10 kDa fragment, and therefore the faint 12 kDa band is not overshadowed by the much more abundant 10 kDa band. Whereas no 12 kDa fragment was detectable in untreated cells, this band was clearly observed upon treatment with MDL 28170 (FIG. 3, lanes 9, 10).

In summary, no significant inhibition of α- or β-secretase cleavage, but an increase in both the 10 and 12 kDa C-terminal fragments was observed upon treatment with MDL 28170, strongly supporting the role of this compound as a γ-secretase inhibitor which inhibits the conversion of the 10 and 12 kDa fragments to the p3 and Aβ peptides, respectively.

IV. MDL 28170 INHIBITS THE PRODUCTION OF Aβ(40) AND p3(40) BUT NOT Aβ(42) AND p3(42)

MDL 28170 had previously been shown to inhibit the secretion of Aβ and p3 and therefore had been suggested to inhibit γ-secretase. This inhibition was observed by immunoprecipitating media from treated cells with a polyclonal antibody raised to synthetic Aβ(1–40) (Higaki et al., (1995) *Neuron*, 14:651–659). Since the vast majority of secreted Aβ and p3 peptides end at amino acid 40, this experiment does not-distinguish whether only the major γ-secretase cleavage at position 40 is inhibited.

Figure 4A:
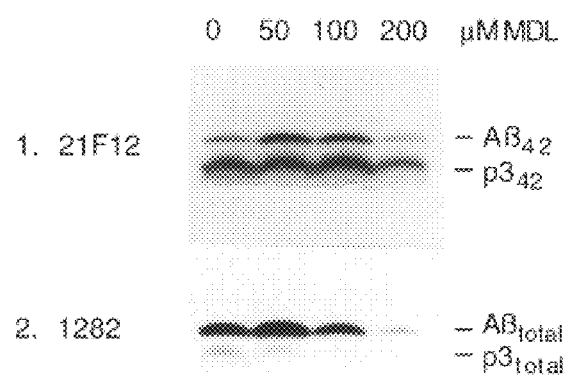
FIGS. 4A–4B. Differential inhibition of Aβ(42) and Aβ(40) formation. (A) Labeled K695sw cells were chased with the indicated concentrations of MDL 28170, and the chase media were precipitated with 21F12 (upper panel) followed by antibody 1282 (lower panel). (B) Quantitation of the effect of 200 μM MDL 28170 on Aβ and p3 in the chase media by phosphorimaging. The bars show the relative pixel number compared to an untreated control (set at 100%). The decreases in Aβ$_{total}$ and p3$_{total}$ relative to an untreated control were significant (*) (two-tailed t-test, n=4, p<0.001), whereas the decreases in Aβ(42) and p3(42) upon treatment with MDL 28170 did not reach significance. The difference in reduction of Aβ(42) level vs. total Aβ level is significant (two-tailed t-test, n=4, p<0.01). The difference in inhibition of p3(42) vs. total p3 is also significant (two-tailed t-test, n=4, p<0.05).
Figure 4B:
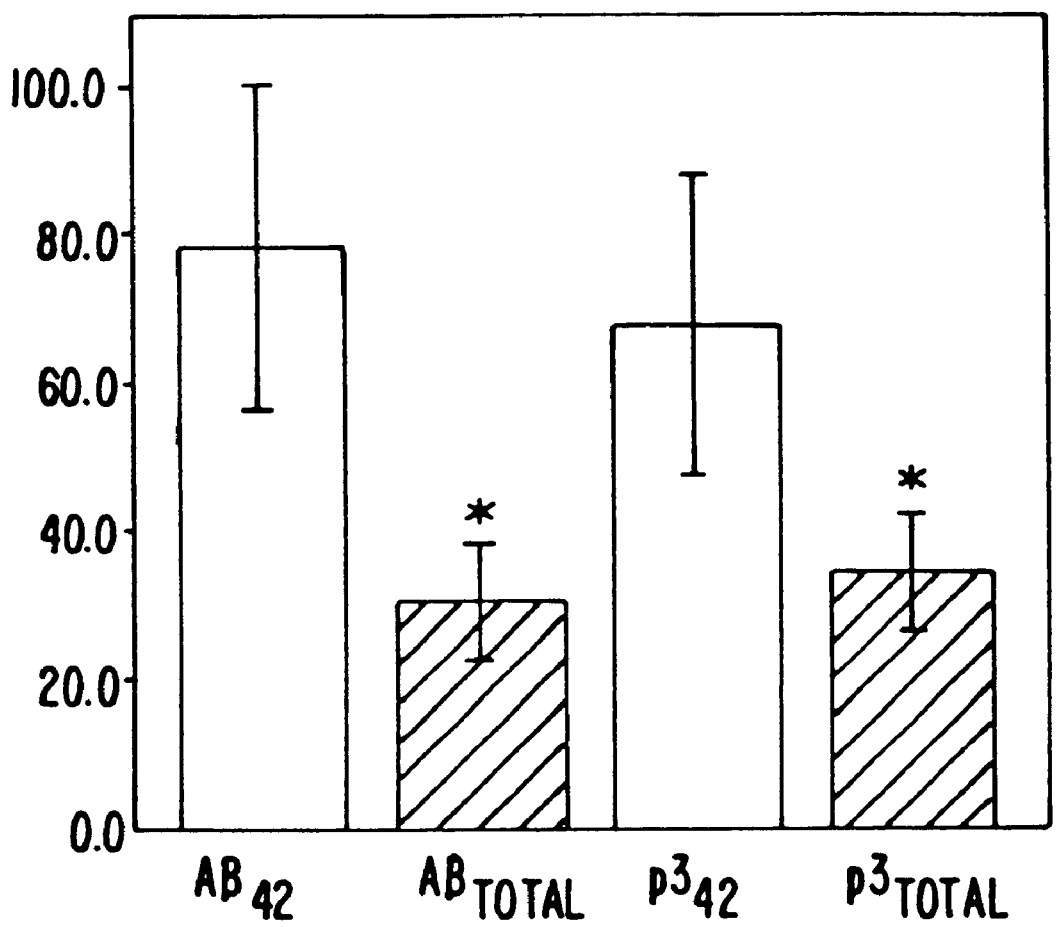

To address this question, we performed pulse-chase experiments on K695sw cells using different doses of MDL 28170, followed by sequential immunoprecipitation of the same media first with 21F12, a monoclonal antibody raised against amino acids 33–42 of Aβ (described above) which specifically precipitates Aβ peptides ending at position 42 and then with antibody 1282 which precipitates all forms of Aβ and p3 (Haass et al., (1992b) *Nature* 359:322–325) (FIG. 4A). Interestingly, 21F12 precipitated not only Aβ, but also p3 peptides, thus demonstrating the existence of secreted p3(42), which had not been described before. Total Aβ and total p3 were strongly and significantly decreased with doses of MDL 28170>50 μM (e.g., at 200 μM p<0.001). In contrast, Aβ(42) and p3(42) showed a bell-shaped dose response curve, with only a small and insignificant decrease at 200 μM, the dose used by Higaki et al. (1995) *Neuron*, 14:651–659, and the highest dose tested here. Using MDL 28170 at 200 μM, the experiment was repeated four times and the results were quantitated by phosphorimaging (FIG. 4B). These data indicate that under the conditions described above the differential effect is significant for both Aβ and p3.

V. DIFFERENTIAL INHIBITION IS ACCOMPLISHED UNDER A NUMBER OF CONDITIONS

Figure 5:
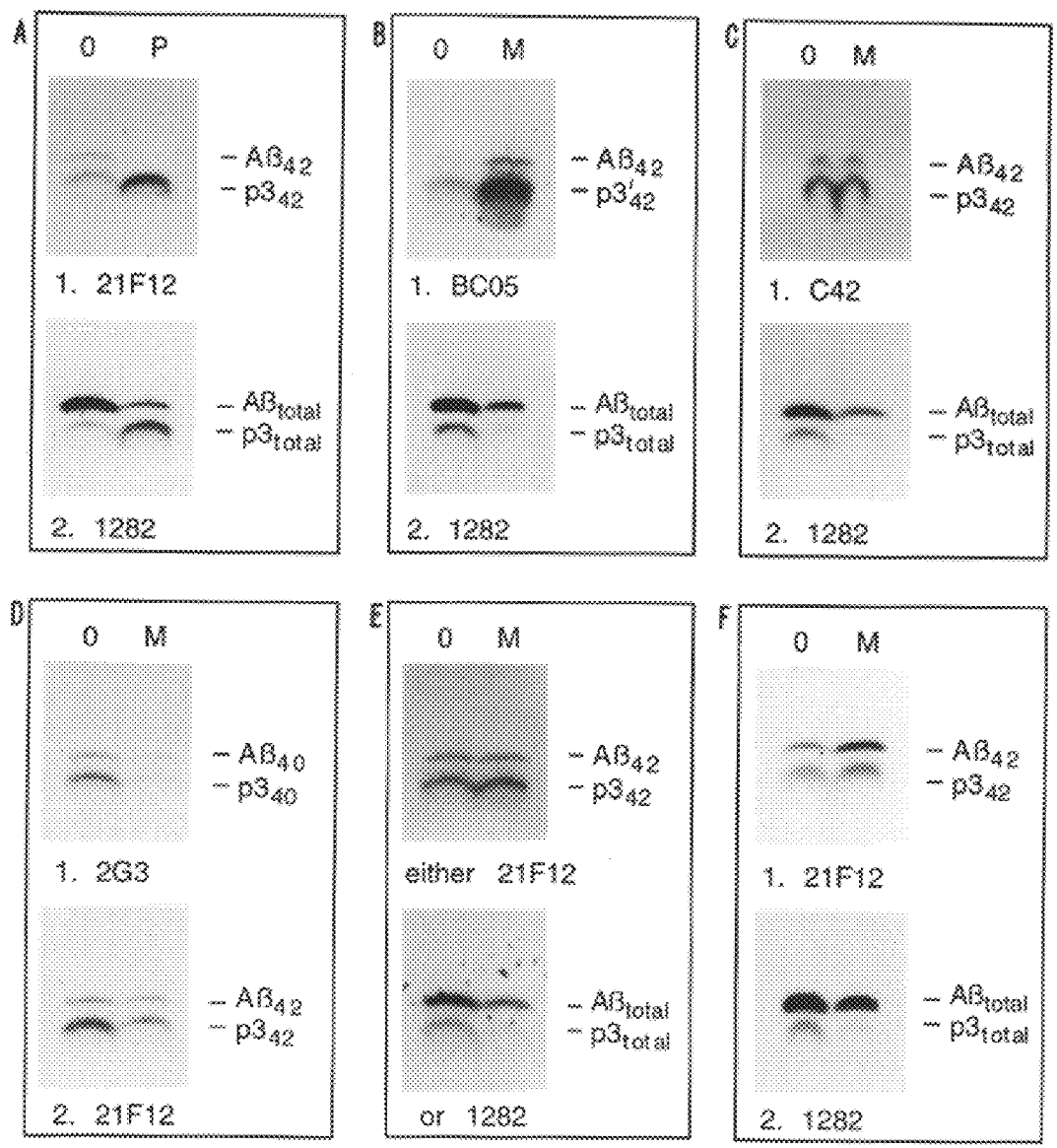
FIGS. 5A–5F. Differential inhibition of Aβ production by K695sw cells under a variety of conditions. (A) treatment with 1 μM PDBu (P) decreases both Aβ(42) and Aβ$_{total}$. Upper panel: antibody 21F12 precipitation, lower panel: subsequent antibody 1282 precipitation. (B–E) K695sw cells were chased with (M) or without (0) 200 μM MDL 28170, and the chase media were immunoprecipitated (B) first with antibody BC05 (upper panel) and then with antibody 1282 (lower panel); (C) first with antibody C42 (upper panel) and then with antibody 1282 (lower panel); (D) first with antibody 2G3 (upper panel) and then with antibody 21F12 (lower panel); (E) after splitting the medium into two aliquots, either with antibody 21F12 (upper panel) or antibody 1282 (lower panel). (F) cells were labeled for 3 h in the presence of 100 μM MDL 28170, and the medium was immunoprecipitated first with antibody 21F12 (upper panel) and then with antibody 1282 (lower panel).

To make sure that the differential effect observed in Aβ(40)/Aβ(42) and p3(40)/p3(42) precipitations is meaningful, we performed a number of control experiments using the K695sw cells. First we treated K695sw cells in a 2 h pulse 2 h chase paradigm with 1 μM of the phorbolester PDBu, which has been shown to decrease total Aβ but increase total p3, probably by diverting βAPP substrate from the β-secretase pathway to the α-secretase route (Buxbaum et al., (1993) "Protein phosphorylation inhibits production of alzheimer amyloid β/A4 peptide," *Proc. Natl. Acad. Sci. USA* 90:9195–9198; Hung et al., (1993) "Activation of protein kinase C inhibits cellular production of the amyloid β-protein," *J. Biol. Chem.* 268:22959–22962). This effect should be independent of the subsequent γ-secretase cleavage and thus the 40 and 42 forms of each metabolite should be equally decreased or increased if the immunoprecipitation paradigm used here works correctly. Indeed, when conditioned media of PDBu-treated cells was precipitated with 21F12, the expected decrease in Aβ(42) and increase in p3(42) were observed indicating that Aβ(42) immunoprecipitation signal does reflect changes in the amounts of precipitable material. Subsequent immunoprecipitation with R1282 shows the same effect for total Aβ and total p3 (FIG. 5A).

The statement that Aβ(42) and p3(42) are not decreased by MDL 28170 depends critically on the quality of the 21F12 antibody. To confirm the effects observed with this antibody, two other previously published Aβ(42)-specific antibodies were used in the pulse chase paradigm with MDL 28170 at 200 μM. The monoclonal antibody BC05 has been extensively used in ELISA assays to detect Aβ(42) (Asami-Odaka et al., (1995) *Biochemistry* 34:10272–10278; Gravina et al., (1995) *J. Biol. Chem.* 270:7013–7016; Suzuki et al., (1994) *Science* 264:1336–1340).

When media from MDL 28170-treated K695sw cells was precipitated with this antibody, we observed an actual increase in both Aβ(42) and p3(42). The subsequent precipitation with R1282 showed the usual decrease in total Aβ and p3 (FIG. 5B).

The polyclonal antibody C42 has also been shown to be specific for Aβ(42) (Saido et al., (1994) Spatial resolution of the primary β-amyloidogenic process induced in postischemic hippocampus. *J. Biol. Chem.* 269:15253–15257). Likewise, this antibody did not show a decrease in Aβ(42) and p3(42) upon treatment whereas the subsequent precipitation with R1282 showed the usual decrease in total Aβ and p3 (FIG. 5C).

The decrease in Aβ(40) and p3(40) was also found when the monoclonal antibody, 2G3 (described above) specific for the free carboxyl-terminus of Aβ(40) and p3(40) was used to precipitate first, followed by 21F12 (FIG. 5D). As expected, the differential inhibition of Aβ production by MDL 28170 was also detected when the precipitations were carried out not sequentially (as described above) but in parallel after the standard pulse-chase. That is, aliquots of media from treated cells and from untreated cells were precipitated with 21F12 for the Aβ42 forms and other aliquots were precipitated with antibody 1282 for total Aβ and total p3. This parallel precipitation produced the same result as the sequential precipitations described above (FIG. 5E).

In summary, three different Aβ(42) end-specific antibodies show that MDL 28170 does not strongly decrease Aβ(42) and p3(42) production whereas a monoclonal antibody to Aβ(40) and p3(40) and different polyclonal antibodies to total Aβ and p3 show a strong decrease. Finally, immunoprecipitation with 21F12 followed by antibody 1282 again revealed this differential inhibition when the inhibitor (100 μM) was applied during a 3 h labeling period instead of in a pulse-chase format (FIG. 5F).

VI. DIFFERENTIAL INHIBITION IS OBSERVED IN SEVERAL CELL LINES

Figure 6:
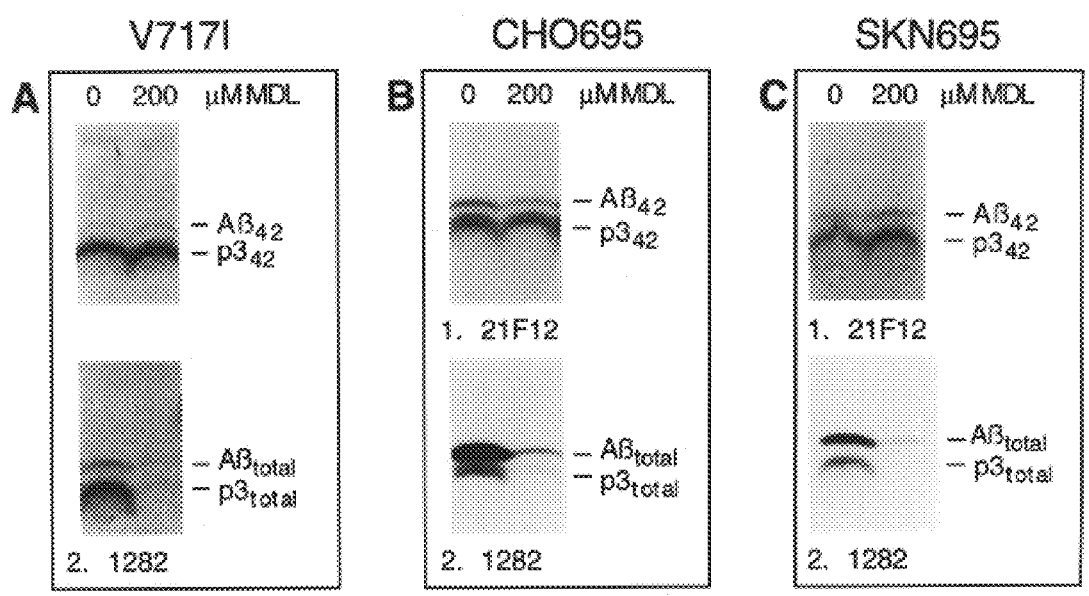
FIGS. 6A–6C. Differential inhibition of Aβ production in different cell types. 35S-methionine labeled cells were chased with the indicated concentrations of MDL 28170 and precipitated with antibody 21F12 (upper panel) followed by antibody 1282 (lower panel). (A) V717F cells. The relatively low APP expression leads to a faint Aβ42 band. (B) CHO695 cells. Note that in CHO cells the p3 brands migrate as doublets, as described (Koo and Squazzo, (1994) "Evidence that production and release of amyloid β-protein involves the endocytic pathway." J. Biol. Chem. 269:17386–17389). (C) SKN695 cells. While Aβ(42) and p3(42) are slightly increased at 200 μM MDL 28170, Aβ$_{total}$ and P3$_{total}$ are decreased.

To check whether the differential inhibition is specific for K695sw, three additional cell lines were treated in the standard 2 h pulse-2 h chase paradigm, and the conditioned media were precipitated first with 21F12 and then with antibody 1282. The kidney cell line K695$_{717}$I expresses APP$_{695}$ carrying the 717I mutation. This line was chosen because it produces increased levels of Aβ(42) due to the mutation (Suzuki et al., (1994) Science 264:1336–1340). At 200 μM MDL 28170, no decrease of Aβ(42) and p3(42) was observed, whereas Aβ(40) and p3(40) were substantially reduced. (FIG. 6A). The Chinese Hamster ovary cell line CHO695 transfected with wild-type βAPP$_{695}$ cDNA was treated with 200 μM MDL 28170 and only a slight decrease of Aβ(42) and p3(42) was observed, whereas Aβ(40) and p3(40) were substantially reduced. (FIG. 6B). The human neuroblastoma cell-line SKN695 expressing wild type βAPP$_{695}$ was treated with 200 μM MDL 28170 (FIG. 6C). While Aβ(42) and p3(42) were slightly increased, total Aβ and total p3 were strongly decreased. Thus, differential inhibition of Aβ(42) vs Aβ(40) and p3(42) vs p3(40) production is not only observed in K695sw but also in a cell line with an Alzheimer's disease linked βAPP717 missense mutation, in a hamster cell line and in a human neural cell line expressing wild type βAPP.

VII. EXPERIMENTAL PROCEDURES

A. Cell Lines

All transfected cell lines described here carry derivatives of pCMV695, a plasmid carrying APP$_{695}$ under control of the CMV promoter (Selkoe, (1988) Proc. Natl. Acad. Sci. 85:7341–7345) K695sw are human embryonic kidney 293 cells stably transfected with a construct carrying the AD-linked double ("Swedish") mutation K595N/M596L (Citron et al. (1992) Nature, 360:672–674); K695$_{717}$, are 293 cells stably transfected with APP$_{695}$ carrying the mutation V717I (valine to isoleucine at position 717 in the APP770 numbering system). CHO695 are Chinese hamster ovary cells (CHO) stably transfected with pCMV695 (Oltersdorf (1990) J. Biol. Chem. 265:4432–4437) SKN695 are SK-N-SH human neuroblastoma cells stably transfected with pCMV695.

B. Pulse-chase Experiments and Immunoprecipitations

To analyze the effect of MDL 28170 on the processing of APP, cells were grown to confluence in two 10 cm dishes, pulse-labeled with 600 μCi of [$^3$S]-methionine in 4 ml of serum-free medium for 2 hours and then chased for 2 hours with 4 ml medium containing 10% fetal bovine serum and the indicated final concentration of MDL 28170 (initially dissolved at 200 mM in DMSO). Control dishes were treated with DMSO alone.

Conditioned media and cell lysates were analyzed by immunoprecipitation, as described (Haass, et al. Nature 359:322–325). Polyclonal antibody R1736 to residues 595–611 of APP$_{695}$, was used to precipitate α-APP$_s$ (Haass, (1994) J. Biol. Chem. 269:17741–17748). This antibody recognizes an epitope that is specific for the free COOH-terminus of α-cleaved APP$_s$. Polyclonal antibody R1282 was generated to synthetic Aβ$_{1-40}$ (Haass, et al. (1992) Nature 359:322–325). This antibody precipitates total Aβ and p3 (and small, variable amounts of APP$_s$) from the media of cultured cells (Haass, et al. (1992) Nature 359:322–325). The monoclonal antibody 2G3 was raised to peptide C(Aminoheptanoic acid)GLMVGGVV (SEQ ID NO:5) and specifically precipitates Aβ(40) and p3(40). Twenty μg of this antibody were used to immunoprecipitate the chase media of 2 dishes. The monoclonal antibody 21F12 was raised to peptide C(Aminoheptanoic acid) GLMVGGVVIA (SEQ ID NO:4) and specifically precipitates Aβ(42) and p3(42). Twenty Aβ of this antibody were used to immunoprecipitate the chase media of 2 dishes. The monoclonal antibody BC05 specifically detects Aβ(42) and p3(42) (Suzuki et al., (1994) Science 264:1336–1340). The polyclonal antibody C7 against the last 20 residues of the APP cytoplasmic tail (Podlisny, (1991) Am. J. Pathol. 138:1423–1435) precipitates N'- and N' plus O'-glycosylated full-length APP as well as its C-terminal proteolytic fragments. The antibody sw192 (Knops et al. (1995) J. Biol. Chem. 270:2419–2422; Haass et al. (1995) Nature Med. 1:1291–1296) specifically precipitates β-cleaved APP$_s$ carrying the Swedish mutation.

SDS-PAGE of immunoprecipitates of cell extracts or of Aβ from media was carried out on 10–20% Tris-Tricine gels (Novex), whereas APP$_s$ precipitates were electrophoresed on 10% SDS-polyacrylamide Tris Glycine gels. All quantitations were performed with a Phosphorimager 400A using Image-QuaNT software (Molecular Dynamics). It should be noted the pulse/chase-immunoprecipitation method allows one to assess any changes in Aβ and p3 simultaneously in the same assay, with each of these peptides being visualized directly in the electrophoretic gel.

VIII. HUMAN NEURONS

Human neurons were cultured as previously described (Seubert et al. Nature (1992) 359:325–327) except that the cells were seeded into 6-well plates in neuronal medium without fetal bovine serum but supplemented with B27 (Gibco). Cells were cultured for 2–3 weeks in serum free medium prior to use.

PDAPP mouse brain cells from 16 day old fetal cerebral cortex were cultured following the protocol for human neurons except the cells were seeded into 24-well plate clusters in neuronal medium with 5% fetal bovine serum (Sigma) and 5% Chang's supplement (Irvine Scientific). Cells were cultured for 5–7 days prior to being used in experiments.

The procedure for examining the effects of substances on Aβ production is as follows. Fresh medium is added to the culture wells and then collected after ~24 (8–30) hrs. This is the "control" sample from each well that the treated sample will be compared to. Fresh medium, containing the substance to be tested is then added and again harvested after a further 24 hr (8–30) incubation. After collection of this "treated" sample, a cytotoxicity assay is performed on the cells. To perform the cytotoxicity assay, cells are incubated in media containing thiazolyl blue (MTT, Sigma) at 1 mg/ml for 15 minutes. The media are then discarded, and the precipitates are analyzed by solubilization in a buffer containing 50% DMF and 20% SDS. The solubilized dye was quantitated on a Molecular Devices Vmax.

Control and treated samples of culture media are assayed for total Aβ using a sandwich ELISA consisting of two monoclonal antibodies. The first antibody 266, specific to amino acids 13–28 of Aβ, is used as a capture antibody (Seubert et al., Nature, supra). The second antibody, 3D6 which is specific to amino acids 1–5 of Aβ, was biotinylated and served as a reporter antibody. The 3D6 biotinylation procedure employed the manufacturer's protocol for NHS-biotin (Pierce) labeling of immunoglobulins, except 100 mM sodium bicarbonate, pH 8.5, buffer was used. The 3D6 antibody does not recognize secreted APP or full-length APP but does recognize Aβ species that begin at position 1.

The samples were also assayed for Aβ(42) with an Aβ(42) specific sandwich ELISA that employed the monoclonal antibody 21F12, which was generated against amino acids 33–42 of Aβ, as the capture antibody. This antibody is specific for longer forms of Aβ since it does not cross-react with Aβ(1–40) in ELISA or competitive radioimmunoassay (RIA). Biotinylated 3D6 is also the reporter antibody in this assay.

The 266 and 21F12 mAbs were coated at 10 μg/ml into 96-well immunoassay plates (Costar) overnight at room temperature. The plates were aspirated and blocked with 0.25% human serum albumin PBS buffer for at least 1 hour at room temperature, then stored desiccated at 4° C. until use. The samples and standards were added to the plates and incubated at room temperature for 1.5 hours.

The biotinylated 3D6 was diluted to 0.5 μg/ml, and incubated in the wells for 1 hour at room temperature. The plates were washed 3 times with wash buffer (Tris buffered saline, 0.05% Tween 20) between each step of the assay. Streptavidin-alkaline phosphatase (Boehringer Mannheim), diluted 1:1000, was added to the wells for the total Aβ assay, and avidin-HRP (Vector) diluted 1:4000 was added to the wells for the Aβ(42) assay. These conjugates were incubated for 1 hour at room temperature. For the total Aβ assay the fluorometric substrate 4-methyl-umbelliferyl phosphate was added to the wells for 30 minutes, then read in a Millipore Cytofluor 2350 fluorometer. The calorimetric substrate, Slow TMB-ELISA (Pierce), was added for the Aβ(42) assay and allowed to react for 15 minutes, after which the enzymatic reaction was stopped with 2N $H_2SO_4$. The plates were read on a Molecular Devices Vmax.

Percent inhibition for both total Aβ and Aβ(42) is defined as:

$$(1-((treated/control_t)/(untreated/control_u)))\times 100\%,$$

where treated=value from treated cells $control_t$=value from the same treated well for the 24 hr period prior to testing untreated=value from well which received no test substance $control_u$=value from the same untreated well for the 24 hr prior to testing It is optimal to divide the values of the treated and untreated samples by their respective values for the 24 hrs prior to the 24 hr test period, as the act of changing the media alone can effect a 5–10% reduction in Aβ production comparing the untreated to $control_u$).

Figure 13A:
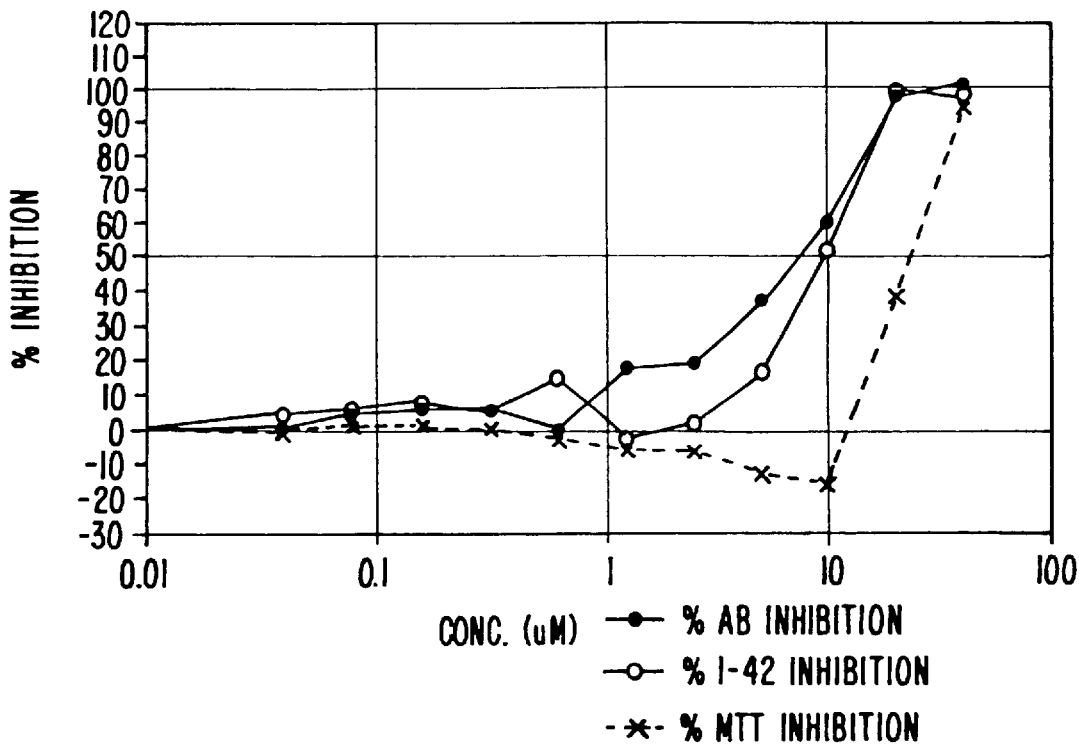
FIGS. 13A–13O depict the percent inhibition of Aβ by several compounds using the brain cell culture method described in Example VIII. The charts show inhibition of total Aβ ("% Aβ inhibition"), inhibition of Aβ(42) ("% 1–42 inhibition") and inhibition of the metabolism of MTT ("% MTT inhibition") (greater inhibition indicates greater cytotoxicity).
Figure 13B:
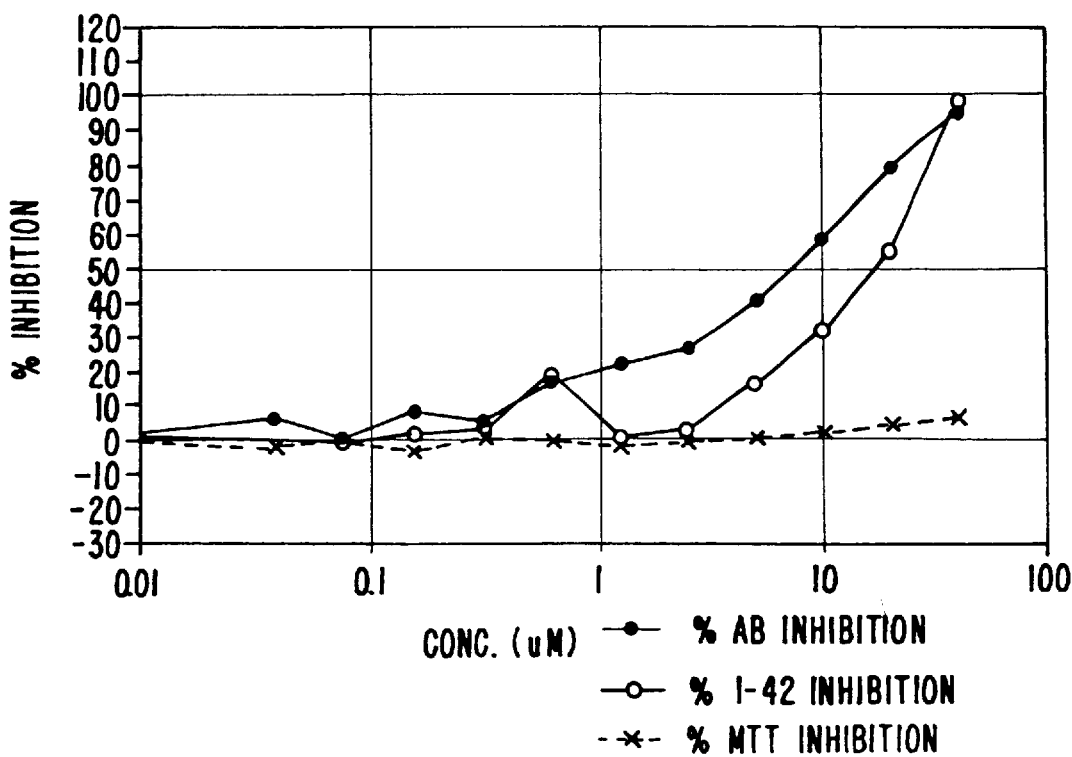
Figure 13C:
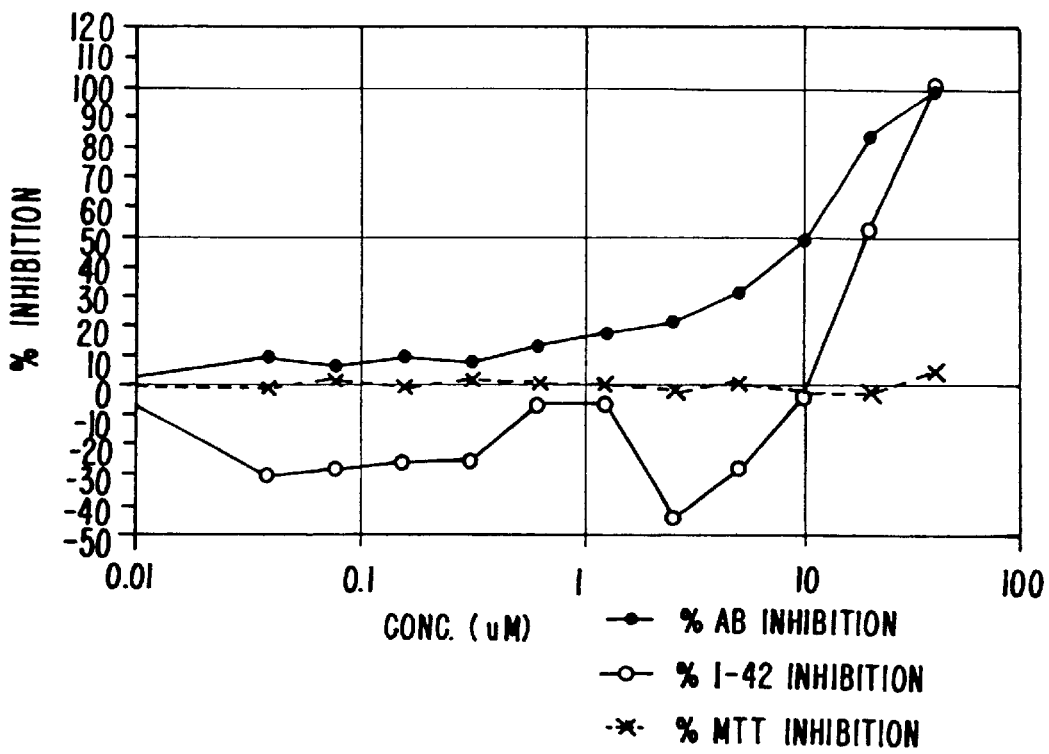
Figure 13D:
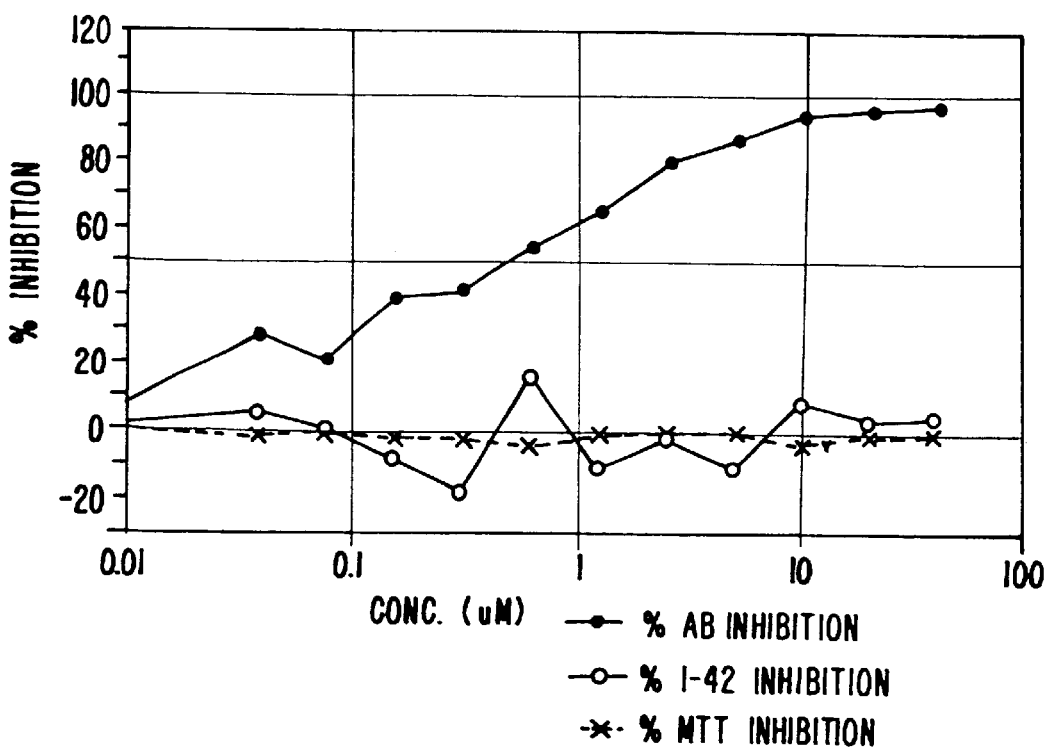
Figure 13E:
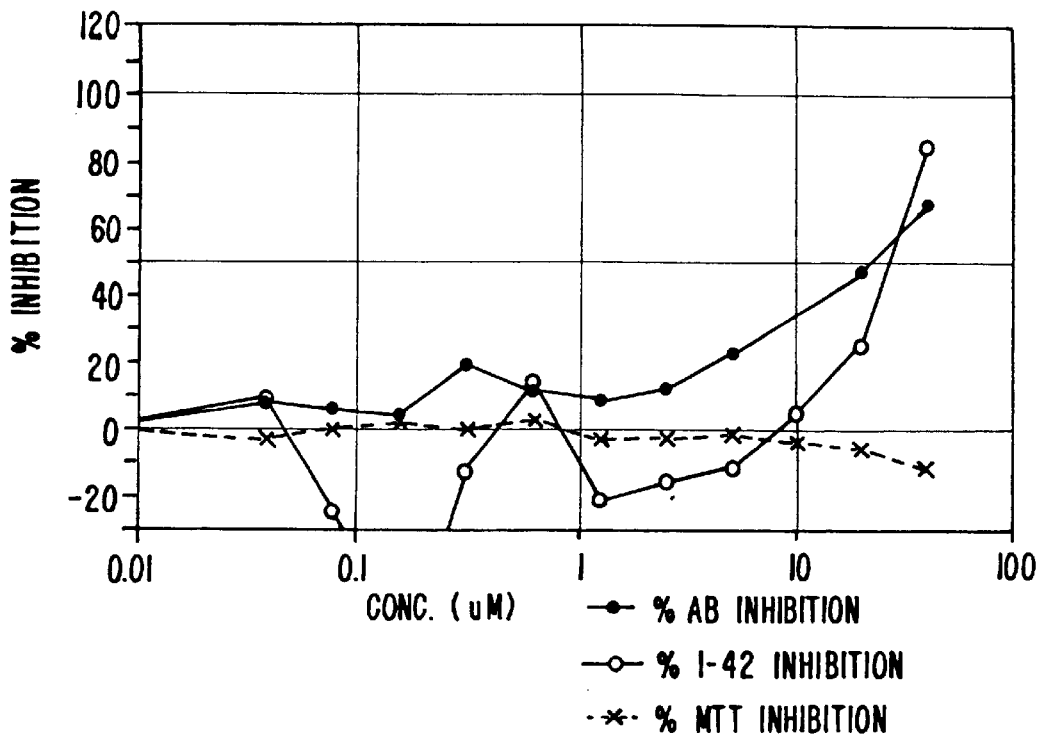
Figure 13F:
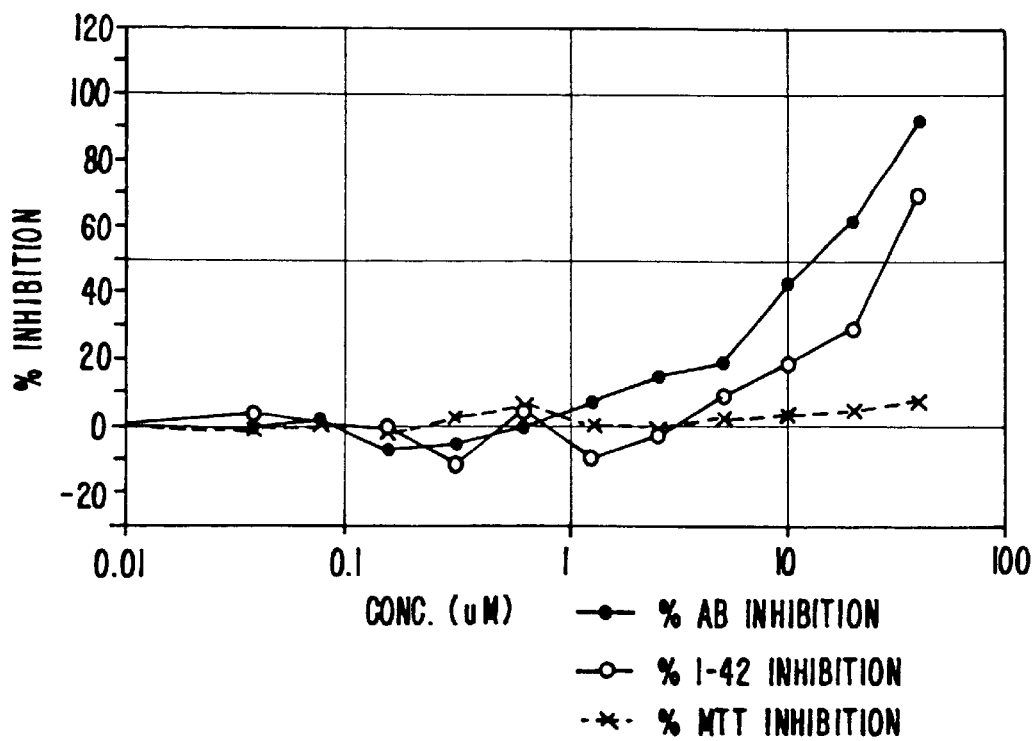
Figure 13G:
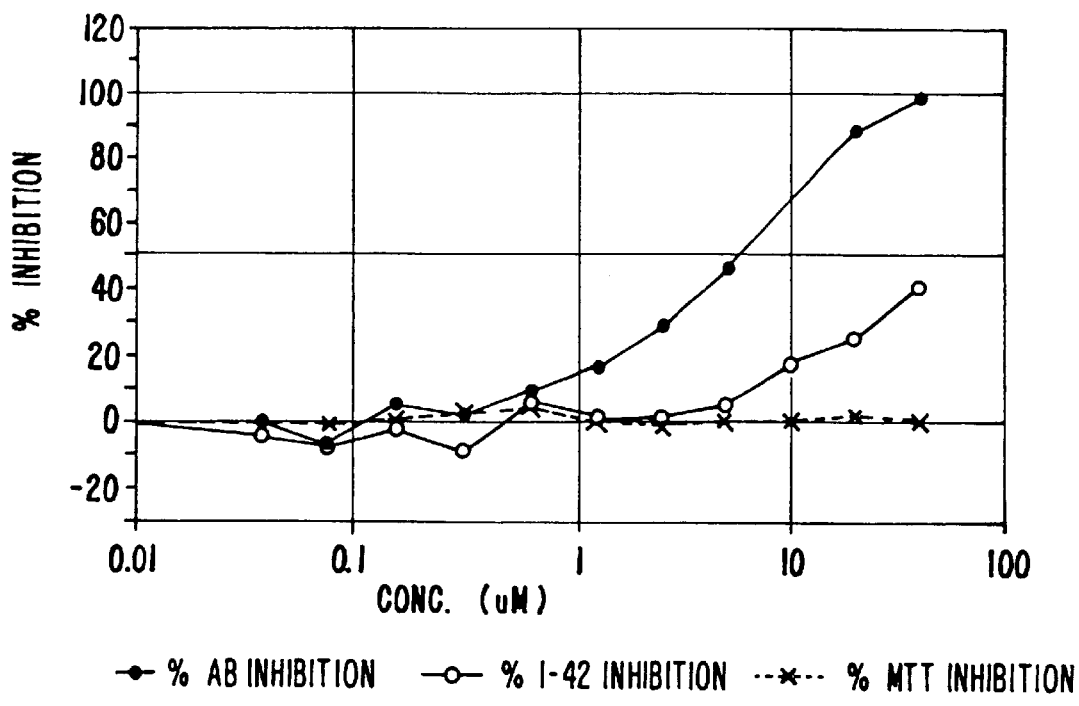
Figure 13H:
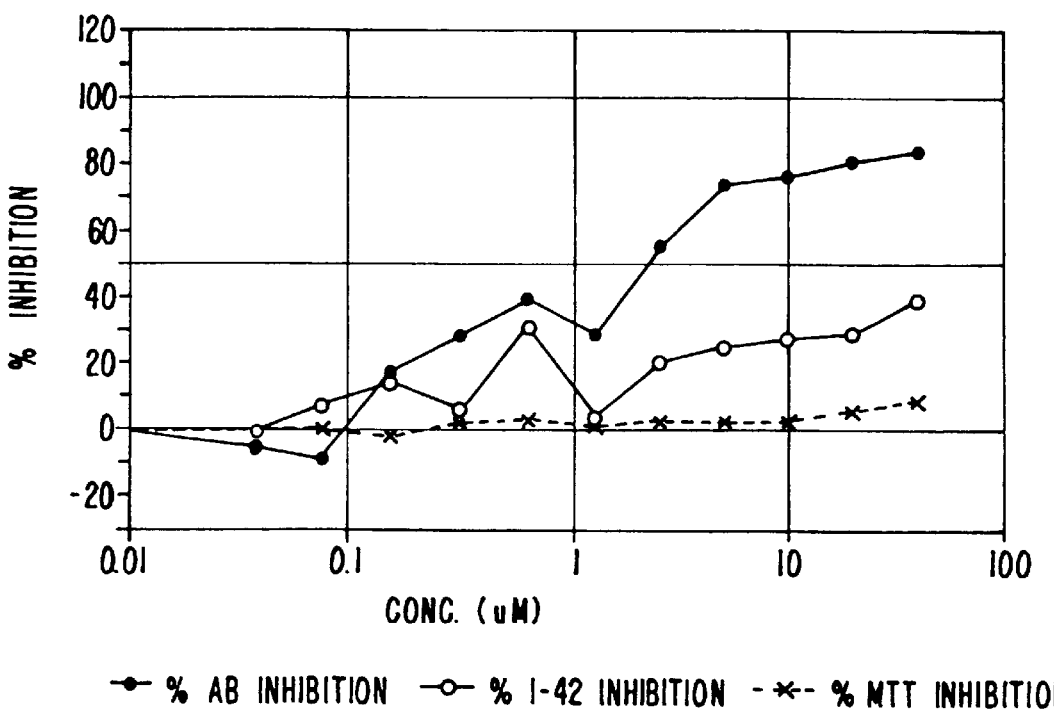
Figure 13I:
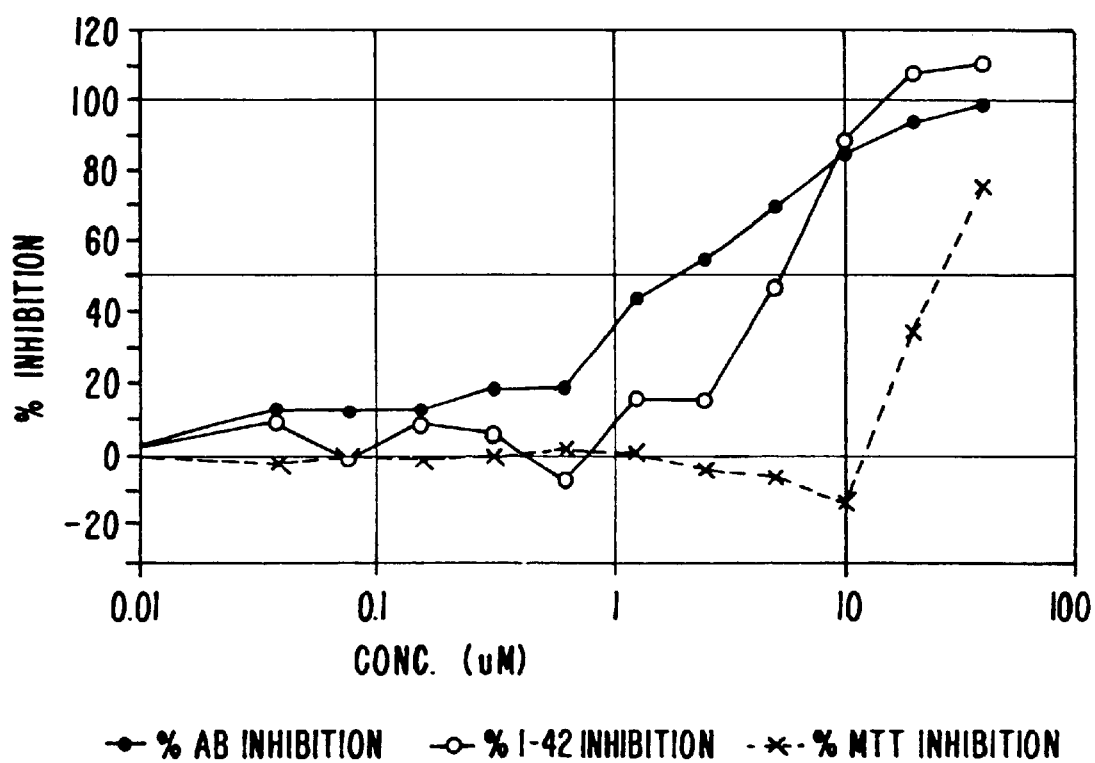
Figure 13J:
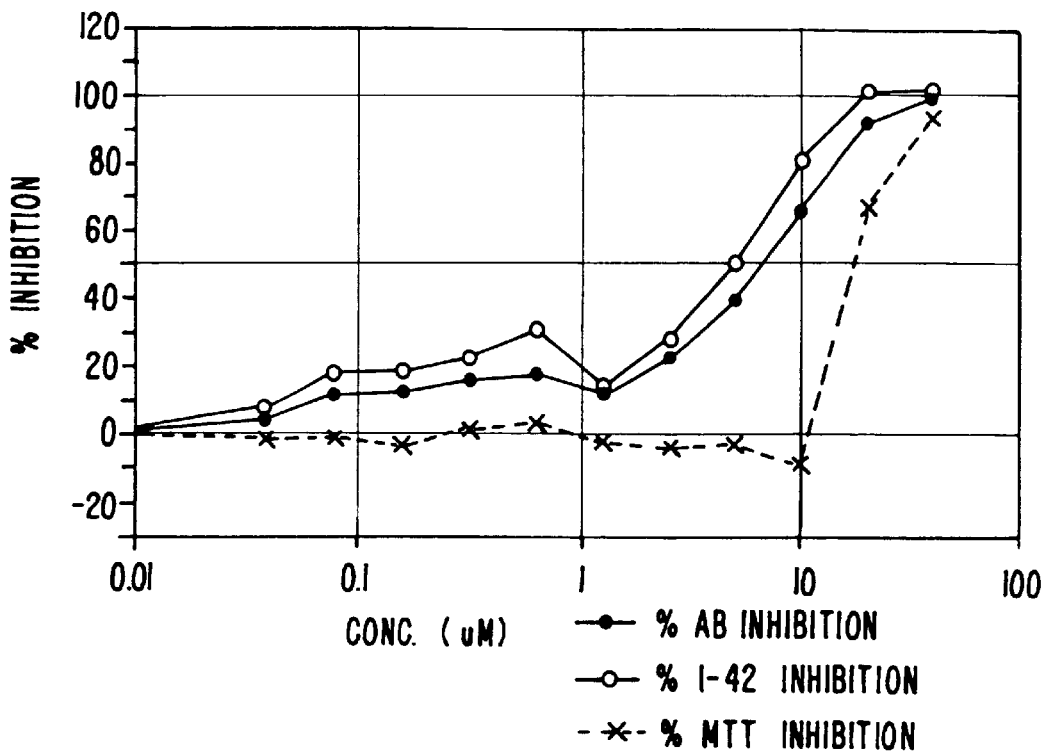
Figure 13K:
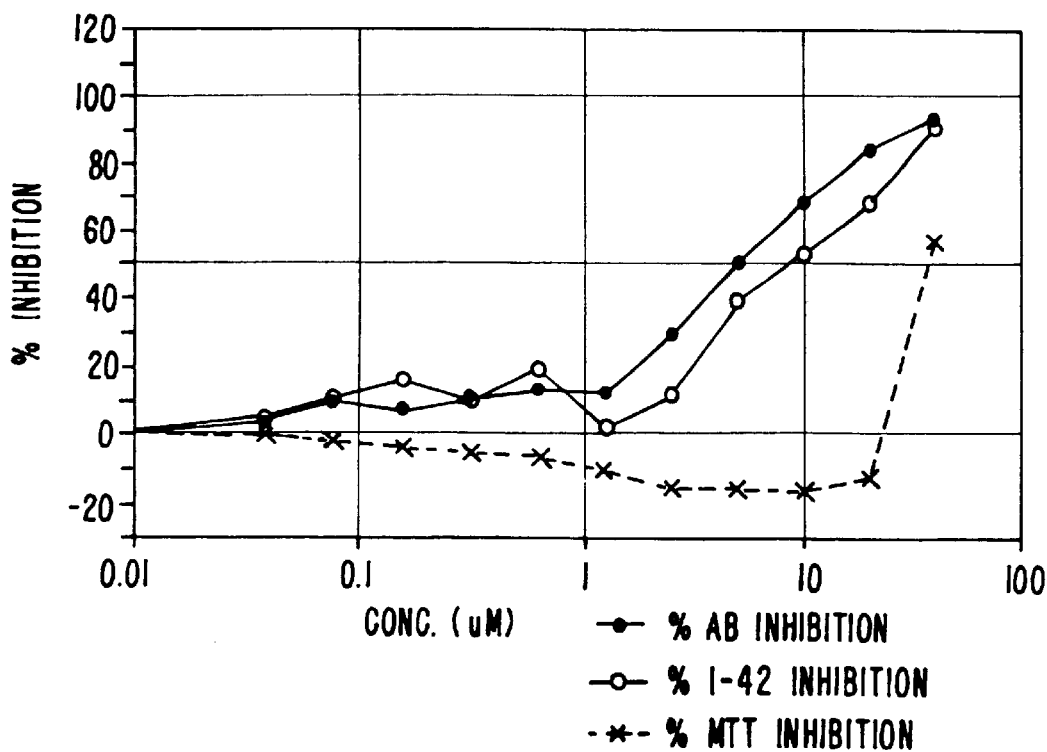
Figure 13L:
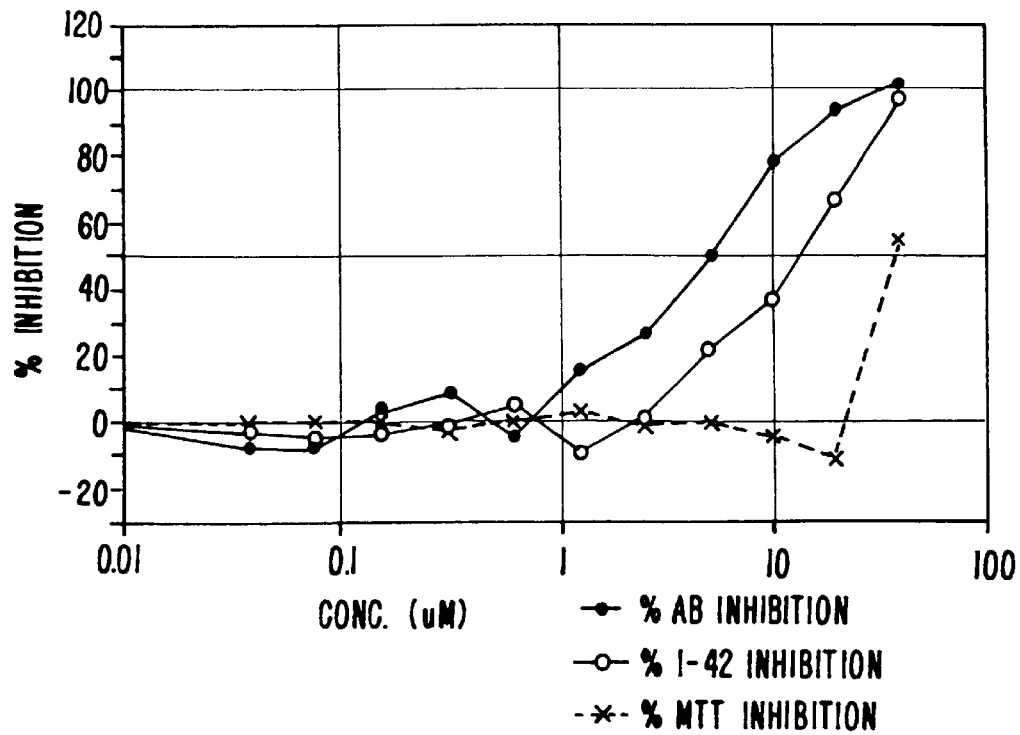
Figure 13M:
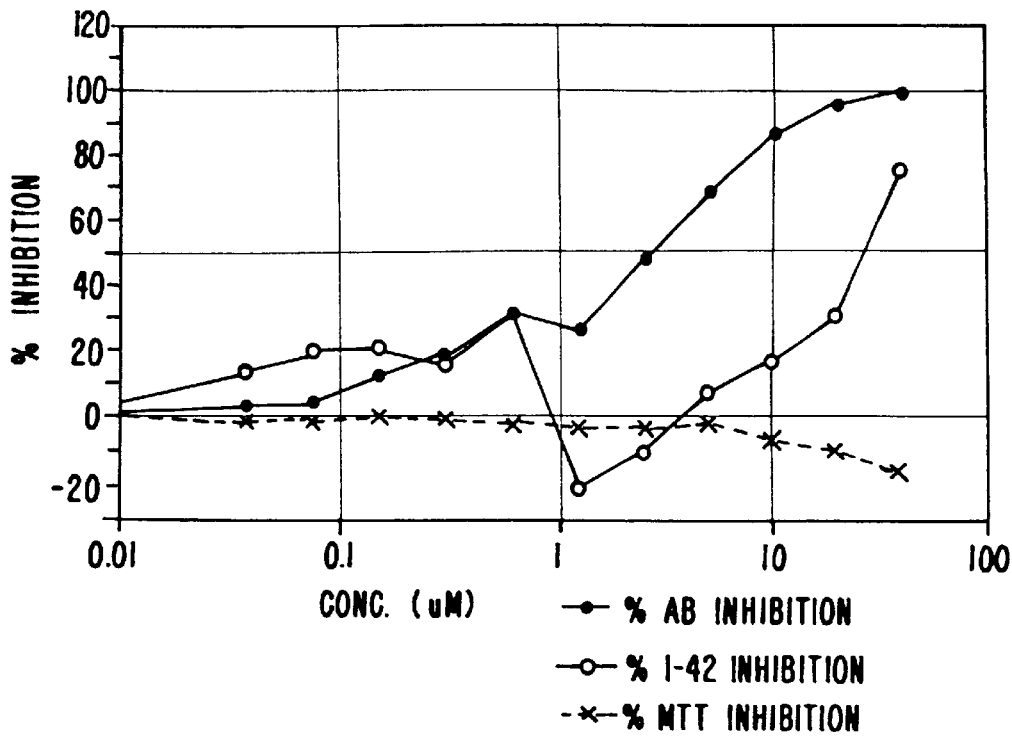
Figure 13N:
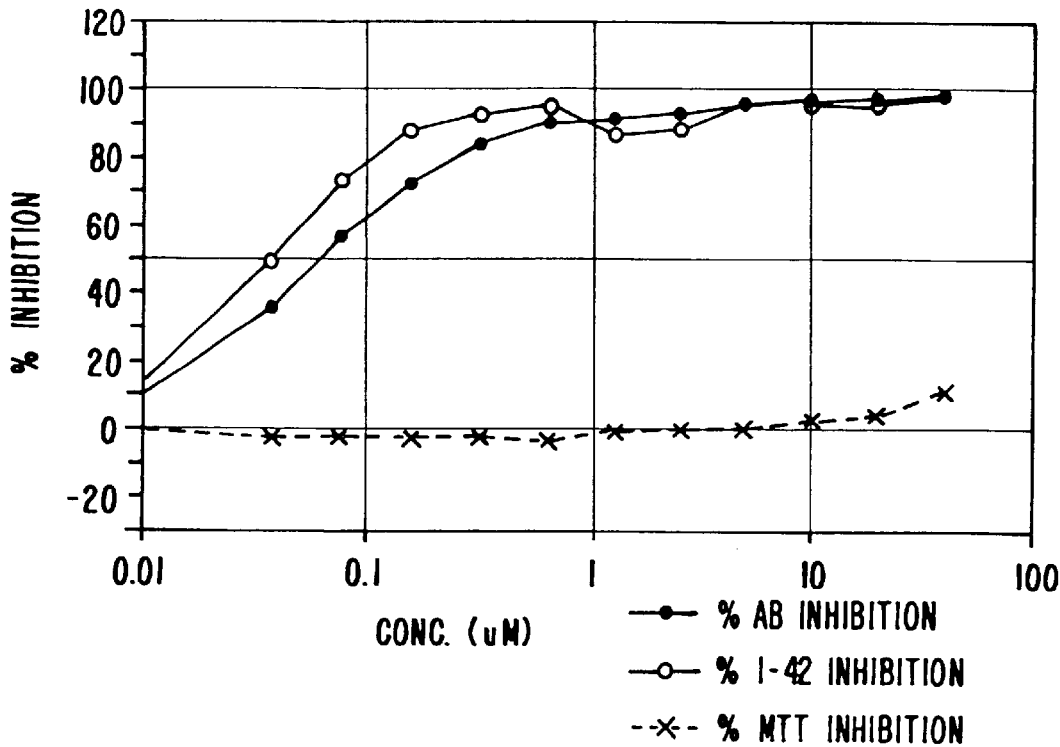
Figure 13O:
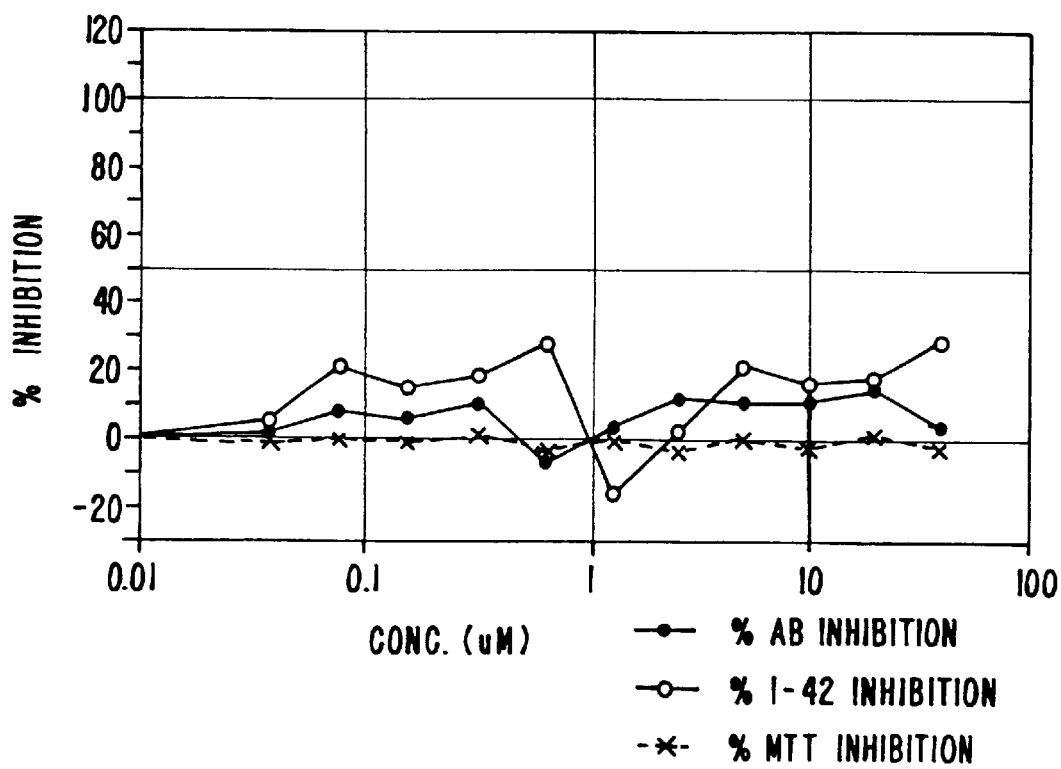

Several compounds were screened for their ability to inhibit both total Aβ and Aβ(42). Results are shown in FIGS. 13A–13O.

IX. PDAPP CONSTRUCT

Figures 8A, 8B:
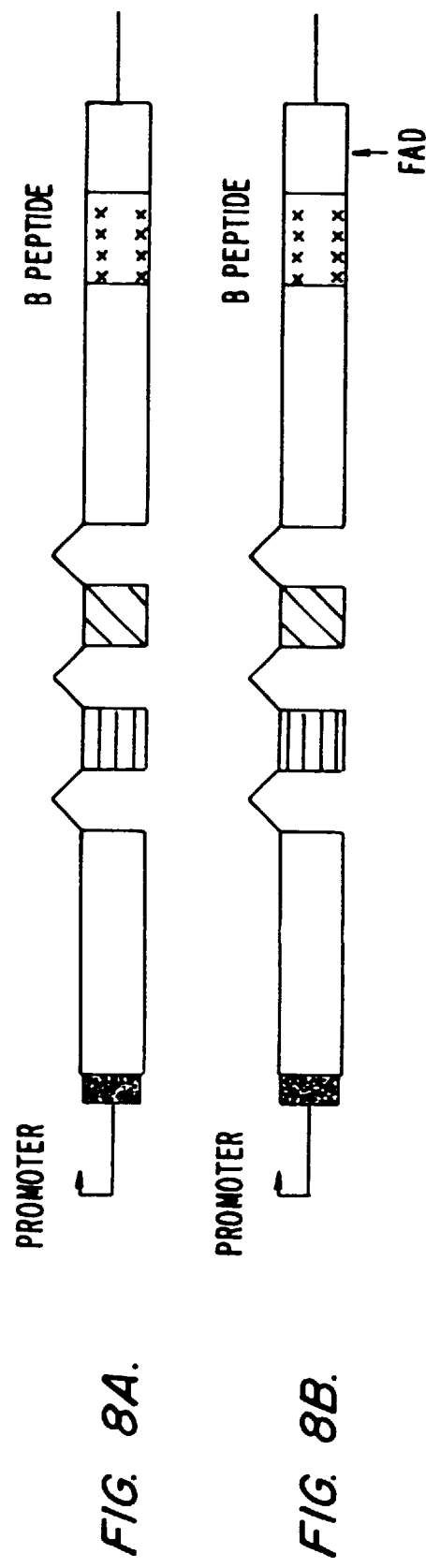
FIG. 8A. Shows a schematic of a combination cDNA/genomic coding sequence allowing alternative splicing of the KPI and OX-2 exons.
FIG. 8B. Shows a schematic of a combination cDNA/genomic coding sequence bearing a mutation at position 717 and allowing alternative splicing of the KPI and OX-2 exons.

A cDNA/genomic APP construct containing introns 6, 7 and 8 is prepared by combining APP cDNA encoding exons 1–6 and 9–18 with genomic APP sequences encoding introns 6, 7 and 8, and exons 7 and 8 (see FIGS. 8A–8B). In order to create a splicing cassette small enough for convenient insertion in a pUC vector, two deletions in intronic sequences are made. A deletion is made in intron 6 from position 143 of intron 6 to the BamHI site located upstream of the beginning of exon 7 (1658 bp before the beginning of exon 7). Another deletion is made in intron 8 from the first BamHI site in intron 8 to a site at 263 bp before the beginning of exon 9. To avoid confusion, these truncated forms of APP introns 6 and 8 are referred to herein as intron A6 and A8. BamHI sites are engineered at the sites of these deletions, so that they are marked by the presence of BamHI sites. In this construct, referred to as PDAPP, exons 7 and 8 and intron 7 are intact genomic sequences, except that the unique XhoI site in intron 7 is destroyed.

DNA fragments containing the truncated introns are generated as follows: a BamHI site is engineered 143 bp into intron 6 nucleotide by PCR mutagenesis ("Mutagenesis by PCR" in *PCR Technology: Current Innovations* (Griffith and Griffith, eds., CRC Press, 1994) pages 69–83) and another BamHI site is engineered by PCR mutagenesis 263 bp prior to the beginning of exon 9. These sites are engineered into separate APP genomic DNA clones containing the junctions of exon 6 and intron 6, and intron 8 and exon 9, respectively, resulting in modified APP genomic DNA clones.

Figure 9:
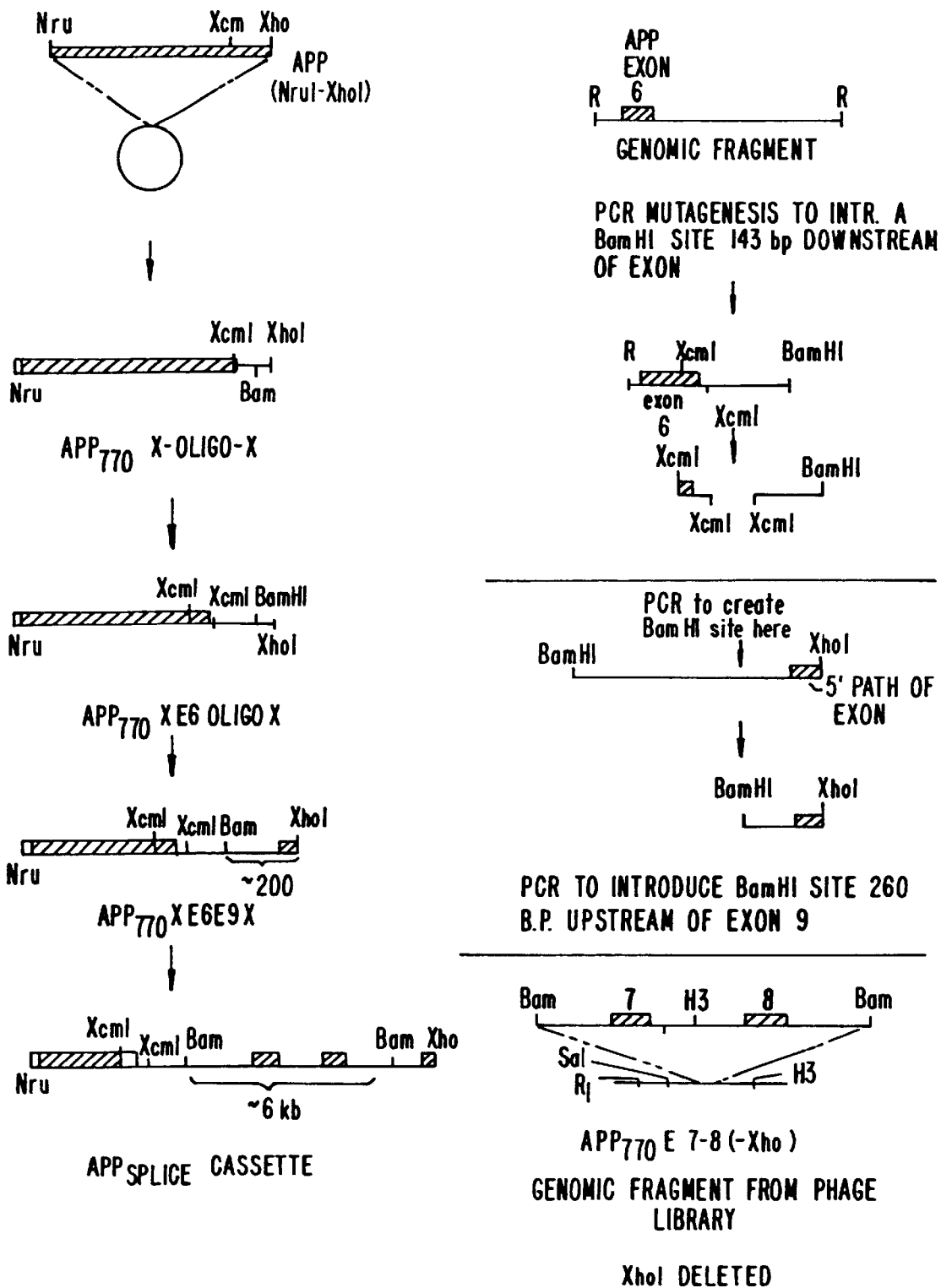
FIG. 9. Diagram of the intermediate constructs used to construct the APP splicing cassette and the PDAPP vector.

The entire cassette is assembled in the APP cDNA clone as follows (FIG. 9). The 889 bp BamHI to XcmI fragment of APP cDNA containing exons 1 through 5 and part of exon 6 (including nucleotides 1 to 843 of FIG. 10 (SEQ ID NO:2)) is cloned into a vector containing BamHI and XhoI sites downstream from the insertion site to make APP770x-oligo-x. APP770x-oligo-x is then cut with XcmI and BamHI. Then two fragments are obtained from the modified APP genomic DNA clone containing the junction of exon 6 and intron 6 described above by cutting with XcmI and BamHI. The resulting 34 bp fragment from the XcmI in exon 6 to the XcmI in intron 6, and 131 bp fragment from the XcmI in intron 6 to the artificially created BamHI site at position 143 bp of intron 6 are ligated into APP770x-oligo-x in a three-way ligation step to make APP 770x-E6oligo-x. The orientation of the fragments are confirmed by sequencing. APP770x-E6oligo-x is then cut with BamHI and XhoI. Then the 313 bp BamHI and XhoI fragment from the modified APP genomic DNA clone containing the junction of intron 8 and exon 9 is ligated into APP770x-E6oligo-x to make APP770xE6E9x.

Figure 11:
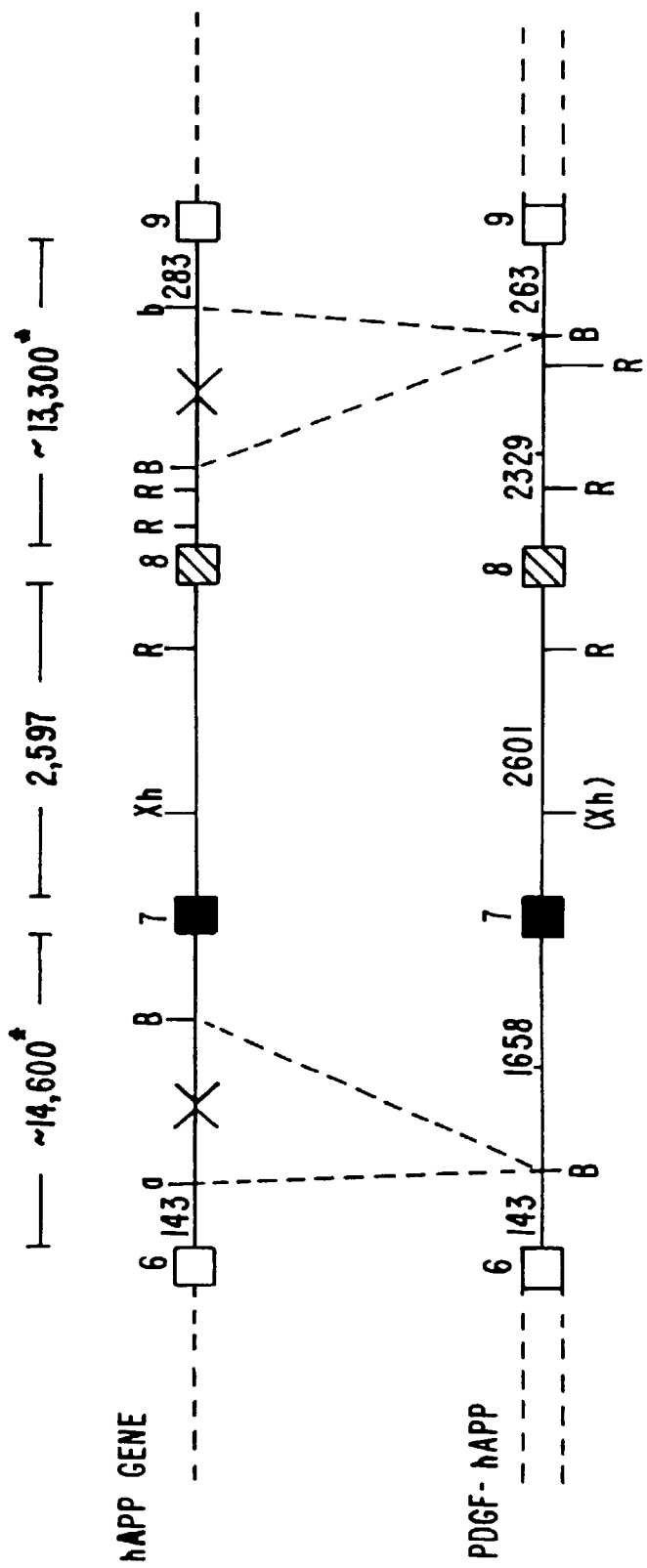
FIG. 11. Diagram of the genomic region of APP present in the PDAPP construct. The sizes of original introns 6, 7 and 8, as well as the sizes of the final introns are indicated in the diagram. The locations of the deletions in introns 6 and 8 present in the PDAPP construct also are indicated.

APP770xE6E9x is then cut with BamHI and the 6.8 kb BamHI fragment of APP genomic DNA encoding the KPI and OX-2 domains (exons 7 and 8) is inserted at this site. This fragment starts at the BamHI site 1658 bp upstream of the start of exon 7 and extends to the first BamHI site in intron 8. This BamHI fragment is obtained from a lambda phage genomic clone encoding this portion of the APP gene, that was obtained from a Human Placental genomic library in the Lambda FIXII vector obtained from Stratagene. This BamHI fragment originally contained an XhoI site which was destroyed by cutting fill in and relegation. The locations of the deletions are diagramed in FIG. 11. This clone, containing exons 1–8 and part of 9, and introns 6, 7 and 8, is termed the "APP splicing cassette." The APP splicing cassette is cut out with NruI and XhoI and used to replace the NruI to XhoI cDNA fragment of APP cDNA bearing a Hardy mutation. This mutant form of APP cDNA is produced by converting the G at nucleotide position 2145 to T by site directed mutagenesis. This changes the encoded amino acid from Val to Phe. The resulting construct is a combination cDNA/genomic APP "minigene."

Sequencing of the 6.8 kb BamHI fragment containing APP exons 7 and 8 derived from the APP genomic clone used to generate this construct showed that intron 7 is 2.6 kb long, and that the first BamHI site in intron 8, the upstream site of the deletion in intron 8 engineered into the APP minigene construct, is 2329 bp downstream from the end of exon 8. This does not coincide with the restriction map of the APP gene published by Yoshikai et al. (1990) and Yoshikai et al. (1991). Comparison of their map to our sequence indicates that Yoshikai et al. switched the order of two EcoRI fragments in their restriction mapping. The 1.60 kb EcoRI fragment containing exon 8 is actually upstream of the 1.48 kb EcoRI fragment and the 1.48 kb EcoRI fragment Yoshikai et al. mapped into intron 7 is actually in intron 8. We have confirmed this location for the EcoRI fragment containing exon 8 by sizing of PCR generated fragments from human DNA.

Figure 12:
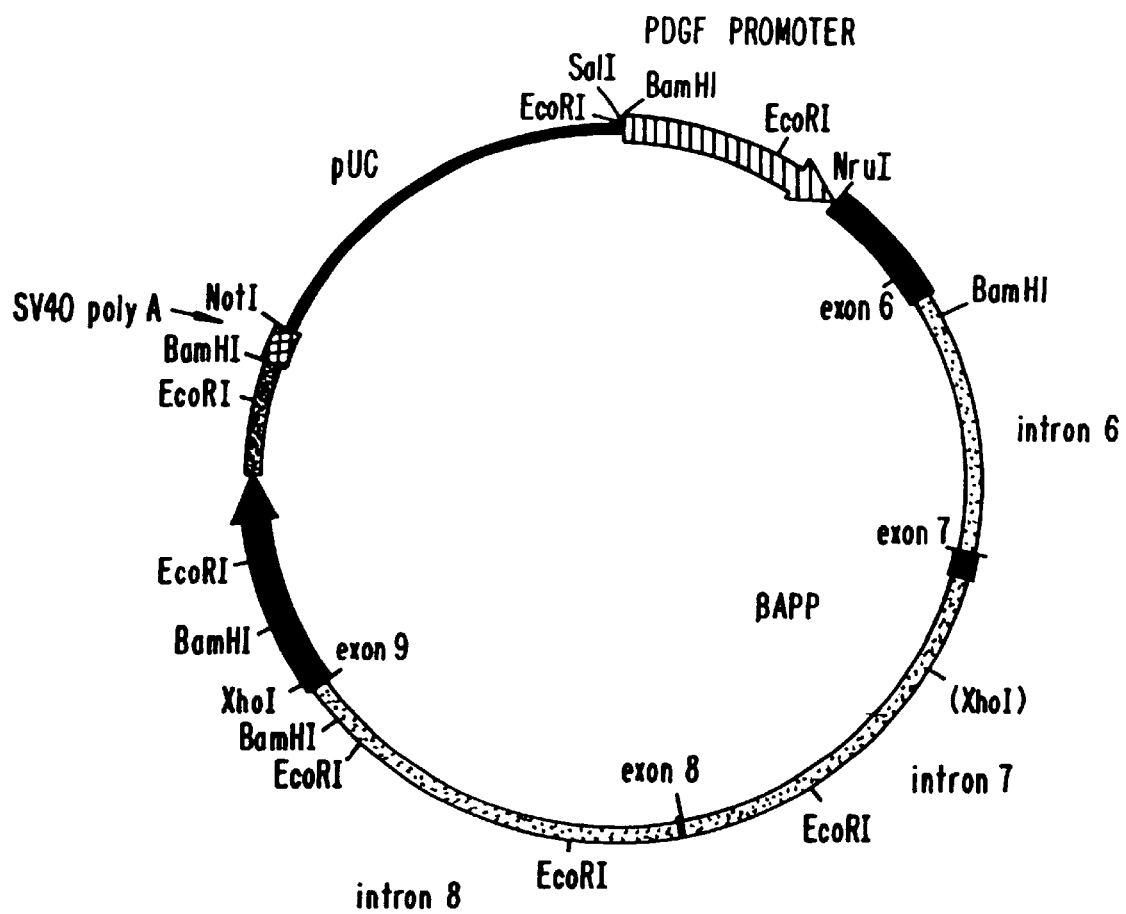
FIG. 12. Schematic map of the PDAPP vector, a combination cDNA/genomic APP construct.

This APP minigene is operatively linked to the PDGF-β promoter to provide expression of the APP cDNA/genomic construct in mammalian cells. The PDGF β-chain 5' flanking sequence is inserted upstream of the NruI site at the beginning of the APP minigene. This fragment includes 1.3 kb upstream of the transcription initiation site, where the PDGF-β promoter resides, and approximately 70 bp of 5' untranslated region, ending at the AurII site (Higgins et al. (1994)). The late SV40 polyadenylation signal, carried on a 240 bp BamHI to BclI fragment, is added downstream of the APP minigene. This construct, combining the PDGF-β promoter, the APP splicing cassette, a Hardy mutation, and the SV40 polyadenylation signal is referred to as PDAPP (FIG. 12).

The present invention provides a novel screening method for determining whether a compound alters the production of Aβ(x–≧41) and/or Aβ(x–≦40) or total Aβ. While specific examples have been provided, the above description is illustrative and not restrictive. Many variations of the invention will become apparent to those of skill in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 43 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:1:

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40
```

(2) INFORMATION FOR SEQ ID NO:2:

(i) SEQUENCE CHARACTERISTICS:
      (A) LENGTH: 2310 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS (B) LOCATION: 1..2310
(D) OTHER INFORMATION: /function= "coding region for APP770"

(xi) SEQUENCE DESCRIPTION: SEQ ID NO:2:

| | | | | | | | | | | | | | | | | |
|---|---|---|---|---|---|---|---|---|---|---|---|---|---|---|---|---|
| ATG | CTG | CCC | GGT | TTG | GCA | CTG | CTC | CTG | CTG | GCC | GCC | TGG | ACG | GCT | CGG | 48 |
| Met | Leu | Pro | Gly | Leu | Ala | Leu | Leu | Leu | Leu | Ala | Ala | Trp | Thr | Ala | Arg | |
| 1 | | | | 5 | | | | | 10 | | | | | 15 | | |

| GCG | CTG | GAG | GTA | CCC | ACT | GAT | GGT | AAT | GCT | GGC | CTG | CTG | GCT | GAA | CCC | 96 |
|---|---|---|---|---|---|---|---|---|---|---|---|---|---|---|---|---|
| Ala | Leu | Glu | Val | Pro | Thr | Asp | Gly | Asn | Ala | Gly | Leu | Leu | Ala | Glu | Pro | |
| | | | 20 | | | | | 25 | | | | | 30 | | | |

| CAG | ATT | GCC | ATG | TTC | TGT | GGC | AGA | CTG | AAC | ATG | CAC | ATG | AAT | GTC | CAG | 144 |
|---|---|---|---|---|---|---|---|---|---|---|---|---|---|---|---|---|
| Gln | Ile | Ala | Met | Phe | Cys | Gly | Arg | Leu | Asn | Met | His | Met | Asn | Val | Gln | |
| | | 35 | | | | | 40 | | | | | 45 | | | | |

| AAT | GGG | AAG | TGG | GAT | TCA | GAT | CCA | TCA | GGG | ACC | AAA | ACC | TGC | ATT | GAT | 192 |
|---|---|---|---|---|---|---|---|---|---|---|---|---|---|---|---|---|
| Asn | Gly | Lys | Trp | Asp | Ser | Asp | Pro | Ser | Gly | Thr | Lys | Thr | Cys | Ile | Asp | |
| | 50 | | | | | 55 | | | | | 60 | | | | | |

| ACC | AAG | GAA | GGC | ATC | CTG | CAG | TAT | TGC | CAA | GAA | GTC | TAC | CCT | GAA | CTG | 240 |
|---|---|---|---|---|---|---|---|---|---|---|---|---|---|---|---|---|
| Thr | Lys | Glu | Gly | Ile | Leu | Gln | Tyr | Cys | Gln | Glu | Val | Tyr | Pro | Glu | Leu | |
| 65 | | | | | 70 | | | | | 75 | | | | | 80 | |

| CAG | ATC | ACC | AAT | GTG | GTA | GAA | GCC | AAC | CAA | CCA | GTG | ACC | ATC | CAG | AAC | 288 |
|---|---|---|---|---|---|---|---|---|---|---|---|---|---|---|---|---|
| Gln | Ile | Thr | Asn | Val | Val | Glu | Ala | Asn | Gln | Pro | Val | Thr | Ile | Gln | Asn | |
| | | | | 85 | | | | | 90 | | | | | 95 | | |

| TGG | TGC | AAG | CGG | GGC | CGC | AAG | CAG | TGC | AAG | ACC | CAT | CCC | CAC | TTT | GTG | 336 |
|---|---|---|---|---|---|---|---|---|---|---|---|---|---|---|---|---|
| Trp | Cys | Lys | Arg | Gly | Arg | Lys | Gln | Cys | Lys | Thr | His | Pro | His | Phe | Val | |
| | | 100 | | | | | 105 | | | | | 110 | | | | |

| ATT | CCC | TAC | CGC | TGC | TTA | GTT | GGT | GAG | TTT | GTA | AGT | GAT | GCC | CTT | CTC | 384 |
|---|---|---|---|---|---|---|---|---|---|---|---|---|---|---|---|---|
| Ile | Pro | Tyr | Arg | Cys | Leu | Val | Gly | Glu | Phe | Val | Ser | Asp | Ala | Leu | Leu | |
| | | 115 | | | | | 120 | | | | | 125 | | | | |

| GTT | CCT | GAC | AAG | TGC | AAA | TTC | TTA | CAC | CAG | GAG | AGG | ATG | GAT | GTT | TGC | 432 |
|---|---|---|---|---|---|---|---|---|---|---|---|---|---|---|---|---|
| Val | Pro | Asp | Lys | Cys | Lys | Phe | Leu | His | Gln | Glu | Arg | Met | Asp | Val | Cys | |
| | 130 | | | | | 135 | | | | | 140 | | | | | |

| GAA | ACT | CAT | CTT | CAC | TGG | CAC | ACC | GTC | GCC | AAA | GAG | ACA | TGC | AGT | GAG | 480 |
|---|---|---|---|---|---|---|---|---|---|---|---|---|---|---|---|---|
| Glu | Thr | His | Leu | His | Trp | His | Thr | Val | Ala | Lys | Glu | Thr | Cys | Ser | Glu | |
| 145 | | | | | 150 | | | | | 155 | | | | | 160 | |

| AAG | AGT | ACC | AAC | TTG | CAT | GAC | TAC | GGC | ATG | TTG | CTG | CCC | TGC | GGA | ATT | 528 |
|---|---|---|---|---|---|---|---|---|---|---|---|---|---|---|---|---|
| Lys | Ser | Thr | Asn | Leu | His | Asp | Tyr | Gly | Met | Leu | Leu | Pro | Cys | Gly | Ile | |
| | | | | 165 | | | | | 170 | | | | | 175 | | |

| GAC | AAG | TTC | CGA | GGG | GTA | GAG | TTT | GTG | TGT | TGC | CCA | CTG | GCT | GAA | GAA | 576 |
|---|---|---|---|---|---|---|---|---|---|---|---|---|---|---|---|---|
| Asp | Lys | Phe | Arg | Gly | Val | Glu | Phe | Val | Cys | Cys | Pro | Leu | Ala | Glu | Glu | |
| | | | 180 | | | | | 185 | | | | | 190 | | | |

| AGT | GAC | AAT | GTG | GAT | TCT | GCT | GAT | GCG | GAG | GAG | GAT | GAC | TCG | GAT | GTC | 624 |
|---|---|---|---|---|---|---|---|---|---|---|---|---|---|---|---|---|
| Ser | Asp | Asn | Val | Asp | Ser | Ala | Asp | Ala | Glu | Glu | Asp | Asp | Ser | Asp | Val | |
| | | 195 | | | | | 200 | | | | | 205 | | | | |

| TGG | TGG | GGC | GGA | GCA | GAC | ACA | GAC | TAT | GCA | GAT | GGG | AGT | GAA | GAC | AAA | 672 |
|---|---|---|---|---|---|---|---|---|---|---|---|---|---|---|---|---|
| Trp | Trp | Gly | Gly | Ala | Asp | Thr | Asp | Tyr | Ala | Asp | Gly | Ser | Glu | Asp | Lys | |
| | 210 | | | | | 215 | | | | | 220 | | | | | |

| GTA | GTA | GAA | GTA | GCA | GAG | GAG | GAA | GAA | GTG | GCT | GAG | GTG | GAA | GAA | GAA | 720 |
|---|---|---|---|---|---|---|---|---|---|---|---|---|---|---|---|---|
| Val | Val | Glu | Val | Ala | Glu | Glu | Glu | Glu | Val | Ala | Glu | Val | Glu | Glu | Glu | |
| 225 | | | | | 230 | | | | | 235 | | | | | 240 | |

| GAA | GCC | GAT | GAT | GAC | GAG | GAC | GAT | GAG | GAT | GGT | GAT | GAG | GTA | GAG | GAA | 768 |
|---|---|---|---|---|---|---|---|---|---|---|---|---|---|---|---|---|
| Glu | Ala | Asp | Asp | Asp | Glu | Asp | Asp | Glu | Asp | Gly | Asp | Glu | Val | Glu | Glu | |
| | | | | 245 | | | | | 250 | | | | | 255 | | |

| GAG | GCT | GAG | GAA | CCC | TAC | GAA | GAA | GCC | ACA | GAG | AGA | ACC | ACC | AGC | ATT | 816 |
|---|---|---|---|---|---|---|---|---|---|---|---|---|---|---|---|---|
| Glu | Ala | Glu | Glu | Pro | Tyr | Glu | Glu | Ala | Thr | Glu | Arg | Thr | Thr | Ser | Ile | |
| | | | 260 | | | | | 265 | | | | | 270 | | | |

| GCC | ACC | ACC | ACC | ACC | ACC | ACA | GAG | TCT | GTG | GAA | GAG | GTG | GTT | CGA | | 864 |
|---|---|---|---|---|---|---|---|---|---|---|---|---|---|---|---|---|
| Ala | Thr | Thr | Thr | Thr | Thr | Thr | Glu | Ser | Val | Glu | Glu | Val | Val | Arg | | |
| | | 275 | | | | | 280 | | | | | 285 | | | | |

| GAG | GTG | TGC | TCT | GAA | CAA | GCC | GAG | ACG | GGG | CCG | TGC | CGA | GCA | ATG | ATC | 912 |
|---|---|---|---|---|---|---|---|---|---|---|---|---|---|---|---|---|

```
                                                                     -continued Glu Val Cys Ser Glu Gln Ala Glu Thr Gly Pro Cys Arg Ala Met Ile
    290                 295                 300

TCC CGC TGG TAC TTT GAT GTG ACT GAA GGG AAG TGT GCC CCA TTC TTT       960
Ser Arg Trp Tyr Phe Asp Val Thr Glu Gly Lys Cys Ala Pro Phe Phe
305                 310                 315                 320

TAC GGC GGA TGT GGC GGC AAC CGG AAC AAC TTT GAC ACA GAA GAG TAC      1008
Tyr Gly Gly Cys Gly Gly Asn Arg Asn Asn Phe Asp Thr Glu Glu Tyr
                325                 330                 335

TGC ATG GCC GTG TGT GGC AGC GCC ATG TCC CAA AGT TTA CTC AAG ACT      1056
Cys Met Ala Val Cys Gly Ser Ala Met Ser Gln Ser Leu Leu Lys Thr
                340                 345                 350

ACC CAG GAA CCT CTT GCC CGA GAT CCT GTT AAA CTT CCT ACA ACA GCA      1104
Thr Gln Glu Pro Leu Ala Arg Asp Pro Val Lys Leu Pro Thr Thr Ala
            355                 360                 365

GCC AGT ACC CCT GAT GCC GTT GAC AAG TAT CTC GAG ACA CCT GGG GAT      1152
Ala Ser Thr Pro Asp Ala Val Asp Lys Tyr Leu Glu Thr Pro Gly Asp
370                 375                 380

GAG AAT GAA CAT GCC CAT TTC CAG AAA GCC AAA GAG AGG CTT GAG GCC      1200
Glu Asn Glu His Ala His Phe Gln Lys Ala Lys Glu Arg Leu Glu Ala
385                 390                 395                 400

AAG CAC CGA GAG AGA ATG TCC CAG GTC ATG AGA GAA TGG GAA GAG GCA      1248
Lys His Arg Glu Arg Met Ser Gln Val Met Arg Glu Trp Glu Glu Ala
                405                 410                 415

GAA CGT CAA GCA AAG AAC TTG CCT AAA GCT GAT AAG AAG GCA GTT ATC      1296
Glu Arg Gln Ala Lys Asn Leu Pro Lys Ala Asp Lys Lys Ala Val Ile
                420                 425                 430

CAG CAT TTC CAG GAG AAA GTG GAA TCT TTG GAA CAG GAA GCA GCC AAC      1344
Gln His Phe Gln Glu Lys Val Glu Ser Leu Glu Gln Glu Ala Ala Asn
            435                 440                 445

GAG AGA CAG CAG CTG GTG GAG ACA CAC ATG GCC AGA GTG GAA GCC ATG      1392
Glu Arg Gln Gln Leu Val Glu Thr His Met Ala Arg Val Glu Ala Met
450                 455                 460

CTC AAT GAC CGC CGC CGC CTG GCC CTG GAG AAC TAC ATC ACC GCT CTG      1440
Leu Asn Asp Arg Arg Arg Leu Ala Leu Glu Asn Tyr Ile Thr Ala Leu
465                 470                 475                 480

CAG GCT GTT CCT CCT CGG CCT CGT CAC GTG TTC AAT ATG CTA AAG AAG      1488
Gln Ala Val Pro Pro Arg Pro Arg His Val Phe Asn Met Leu Lys Lys
                485                 490                 495

TAT GTC CGC GCA GAA CAG AAG GAC AGA CAG CAC ACC CTA AAG CAT TTC      1536
Tyr Val Arg Ala Glu Gln Lys Asp Arg Gln His Thr Leu Lys His Phe
                500                 505                 510

GAG CAT GTG CGC ATG GTG GAT CCC AAG AAA GCC GCT CAG ATC CGG TCC      1584
Glu His Val Arg Met Val Asp Pro Lys Lys Ala Ala Gln Ile Arg Ser
            515                 520                 525

CAG GTT ATG ACA CAC CTC CGT GTG ATT TAT GAG CGC ATG AAT CAG TCT      1632
Gln Val Met Thr His Leu Arg Val Ile Tyr Glu Arg Met Asn Gln Ser
530                 535                 540

CTC TCC CTG CTC TAC AAC GTG CCT GCA GTG GCC GAG GAG ATT CAG GAT      1680
Leu Ser Leu Leu Tyr Asn Val Pro Ala Val Ala Glu Glu Ile Gln Asp
545                 550                 555                 560

GAA GTT GAT GAG CTG CTT CAG AAA GAG CAA AAC TAT TCA GAT GAC GTC      1728
Glu Val Asp Glu Leu Leu Gln Lys Glu Gln Asn Tyr Ser Asp Asp Val
                565                 570                 575

TTG GCC AAC ATG ATT AGT GAA CCA AGG ATC AGT TAC GGA AAC GAT GCT      1776
Leu Ala Asn Met Ile Ser Glu Pro Arg Ile Ser Tyr Gly Asn Asp Ala
                580                 585                 590

CTC ATG CCA TCT TTG ACC GAA ACG AAA ACC ACC GTG GAG CTC CTT CCC      1824
Leu Met Pro Ser Leu Thr Glu Thr Lys Thr Thr Val Glu Leu Leu Pro
            595                 600                 605
```

-continued

```
GTG AAT GGA GAG TTC AGC CTG GAC GAT CTC CAG CCG TGG CAT TCT TTT       1872
Val Asn Gly Glu Phe Ser Leu Asp Asp Leu Gln Pro Trp His Ser Phe
610                 615                 620

GGG GCT GAC TCT GTG CCA GCC AAC ACA GAA AAC GAA GTT GAG CCT GTT       1920
Gly Ala Asp Ser Val Pro Ala Asn Thr Glu Asn Glu Val Glu Pro Val
625                 630                 635                 640

GAT GCC CGC CCT GCT GCC GAC CGA GGA CTG ACC ACT CGA CCA GGT TCT       1968
Asp Ala Arg Pro Ala Ala Asp Arg Gly Leu Thr Thr Arg Pro Gly Ser
                645                 650                 655

GGG TTG ACA AAT ATC AAG ACG GAG GAG ATC TCT GAA GTG AAG ATG GAT       2016
Gly Leu Thr Asn Ile Lys Thr Glu Glu Ile Ser Glu Val Lys Met Asp
                660                 665                 670

GCA GAA TTC CGA CAT GAC TCA GGA TAT GAA GTT CAT CAT CAA AAA TTG       2064
Ala Glu Phe Arg His Asp Ser Gly Tyr Glu Val His His Gln Lys Leu
                675                 680                 685

GTG TTC TTT GCA GAA GAT GTG GGT TCA AAC AAA GGT GCA ATC ATT GGA       2112
Val Phe Phe Ala Glu Asp Val Gly Ser Asn Lys Gly Ala Ile Ile Gly
                690                 695                 700

CTC ATG GTG GGC GGT GTT GTC ATA GCG ACA GTG ATC GTC ATC ACC TTG       2160
Leu Met Val Gly Gly Val Val Ile Ala Thr Val Ile Val Ile Thr Leu
705                 710                 715                 720

GTG ATG CTG AAG AAG AAA CAG TAC ACA TCC ATT CAT CAT GGT GTG GTG       2208
Val Met Leu Lys Lys Lys Gln Tyr Thr Ser Ile His His Gly Val Val
                725                 730                 735

GAG GTT GAC GCC GCT GTC ACC CCA GAG GAG CGC CAC CTG TCC AAG ATG       2256
Glu Val Asp Ala Ala Val Thr Pro Glu Glu Arg His Leu Ser Lys Met
                740                 745                 750

CAG CAG AAC GGC TAC GAA AAT CCA ACC TAC AAG TTC TTT GAG CAG ATG       2304
Gln Gln Asn Gly Tyr Glu Asn Pro Thr Tyr Lys Phe Phe Glu Gln Met
                755                 760                 765

CAG AAC                                                                2310
Gln Asn
    770
```

(2) INFORMATION FOR SEQ ID NO:3:

(i) SEQUENCE CHARACTERISTICS:
        (A) LENGTH: 770 amino acids
        (B) TYPE: amino acid
        (D) TOPOLOGY: linear (ii) MOLECULE TYPE: protein (xi) SEQUENCE DESCRIPTION: SEQ ID NO:3:

```
Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125
```

-continued

```
Val Pro Asp Lys Cys Lys Phe Leu His Gln Glu Arg Met Asp Val Cys
    130                 135                 140
Glu Thr His Leu His Trp His Thr Val Ala Lys Glu Thr Cys Ser Glu
145                 150                 155                 160
Lys Ser Thr Asn Leu His Asp Tyr Gly Met Leu Leu Pro Cys Gly Ile
                165                 170                 175
Asp Lys Phe Arg Gly Val Glu Phe Val Cys Cys Pro Leu Ala Glu Glu
            180                 185                 190
Ser Asp Asn Val Asp Ser Ala Asp Ala Glu Glu Asp Asp Ser Asp Val
        195                 200                 205
Trp Trp Gly Gly Ala Asp Thr Asp Tyr Ala Asp Gly Ser Glu Asp Lys
    210                 215                 220
Val Val Glu Val Ala Glu Glu Glu Val Ala Glu Val Glu Glu Glu
225                 230                 235                 240
Glu Ala Asp Asp Glu Asp Asp Glu Asp Gly Asp Glu Val Glu Glu
                245                 250                 255
Glu Ala Glu Glu Pro Tyr Glu Glu Ala Thr Glu Arg Thr Thr Ser Ile
            260                 265                 270
Ala Thr Thr Thr Thr Thr Thr Glu Ser Val Glu Glu Val Val Arg
    275                 280                 285
Glu Val Cys Ser Glu Gln Ala Glu Thr Gly Pro Cys Arg Ala Met Ile
    290                 295                 300
Ser Arg Trp Tyr Phe Asp Val Thr Glu Gly Lys Cys Ala Pro Phe Phe
305                 310                 315                 320
Tyr Gly Gly Cys Gly Gly Asn Arg Asn Asn Phe Asp Thr Glu Glu Tyr
                325                 330                 335
Cys Met Ala Val Cys Gly Ser Ala Met Ser Gln Ser Leu Leu Lys Thr
            340                 345                 350
Thr Gln Glu Pro Leu Ala Arg Asp Pro Val Lys Leu Pro Thr Thr Ala
        355                 360                 365
Ala Ser Thr Pro Asp Ala Val Asp Lys Tyr Leu Glu Thr Pro Gly Asp
    370                 375                 380
Glu Asn Glu His Ala His Phe Gln Lys Ala Lys Glu Arg Leu Glu Ala
385                 390                 395                 400
Lys His Arg Glu Arg Met Ser Gln Val Met Arg Glu Trp Glu Glu Ala
                405                 410                 415
Glu Arg Gln Ala Lys Asn Leu Pro Lys Ala Asp Lys Lys Ala Val Ile
            420                 425                 430
Gln His Phe Gln Glu Lys Val Glu Ser Leu Glu Gln Glu Ala Ala Asn
        435                 440                 445
Glu Arg Gln Gln Leu Val Glu Thr His Met Ala Arg Val Glu Ala Met
    450                 455                 460
Leu Asn Asp Arg Arg Arg Leu Ala Leu Glu Asn Tyr Ile Thr Ala Leu
465                 470                 475                 480
Gln Ala Val Pro Pro Arg Pro Arg His Val Phe Asn Met Leu Lys Lys
                485                 490                 495
Tyr Val Arg Ala Glu Gln Lys Asp Arg Gln His Thr Leu Lys His Phe
            500                 505                 510
Glu His Val Arg Met Val Asp Pro Lys Lys Ala Ala Gln Ile Arg Ser
        515                 520                 525
Gln Val Met Thr His Leu Arg Val Ile Tyr Glu Arg Met Asn Gln Ser
    530                 535                 540
```

```
Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
                580                 585                 590

Leu Met Pro Ser Leu Thr Glu Thr Lys Thr Thr Val Glu Leu Leu Pro
            595                 600                 605

Val Asn Gly Glu Phe Ser Leu Asp Asp Leu Gln Pro Trp His Ser Phe
        610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
                660                 665                 670

Ala Glu Phe Arg His Asp Ser Gly Tyr Glu Val His His Gln Lys Leu
                675                 680                 685

Val Phe Phe Ala Glu Asp Val Gly Ser Asn Lys Gly Ala Ile Ile Gly
                690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
                740                 745                 750

Gln Gln Asn Gly Tyr Glu Asn Pro Thr Tyr Lys Phe Phe Glu Gln Met
            755                 760                 765

Gln Asn
770

(2) INFORMATION FOR SEQ ID NO:4:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "Xaa = NH - CH-2 - (CH-2)-5
            - CO in an amine linkage between amino acid Cys in
            position 1 and amino acid Gly in position 3"

(xi) SEQUENCE DESCRIPTION: SEQ ID NO:4:

Cys Xaa Gly Leu Met Val Gly Gly Val Val Ile Ala
1               5                   10

(2) INFORMATION FOR SEQ ID NO:5:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide
```

-continued

```
    (ix) FEATURE:
        (A) NAME/KEY: Modified-site
        (B) LOCATION: 2
        (D) OTHER INFORMATION: /note= "Xaa = NH - CH-2 - (CH-2)-5
            - CO in an amine linkage between amino acid Cys in
            position 1 and amino acid Gly in position 3"

(xi) SEQUENCE DESCRIPTION: SEQ ID NO:5:

Cys Xaa Gly Leu Met Val Gly Gly Val Val
1               5                   10
```

What is claimed is:

1. A method for identifying a compound that differentially alters the amount of at least one Aβ(x–$\geq$41) peptide produced by a cell compared with the amount of either total Aβ or at least one Aβ(x–$\leq$40) peptide produced by the cell comprising:

administering a compound to a culture comprising the cell;

measuring the amount of soluble Aβ(x–$\geq$41) peptide, specifically, in a sample from the culture;

determining a first degree of alteration between the amount of the soluble Aβ(x–$\geq$41) peptide and an amount from a culture comprising the cell to which the compound has been administered;

measuring the amount of total soluble Aβ or soluble Aβ(x–$\leq$40) peptide, specifically, in a sample from the culture;

determining a second degree of alteration between the amount of total soluble Aβ or the soluble Aβ(x–$\leq$40) peptide and an amount from a culture comprising the cell to which the compound has been administered; and correlating a statistically significant difference between the first degree of alteration and the second degree of alteration with the ability of the compound to differentially alter the amount of at least one Aβ(x–$\geq$41) peptide produced by a cell compared with the amount of either total Aβ or at least one Aβ(x–$\leq$40) peptide produced by the cell.

2. The method of claim 1 wherein the amount of the Aβ(x–$\geq$41) peptide and the amount of total Aβ or the Aβ(x–$\leq$40) peptide are measured by immunoassay.

3. The method of claim 2 wherein the immunoassay is a sandwich immunoassay comprising capture binding substances bound to a solid phase and labeled detection binding substances.

4. The method of claim 3 wherein the capture binding substance for measuring the amount of the Aβ(x–$\geq$41) peptides are specific for Aβ(x–$\geq$41) peptides.

5. The method of claim 4 wherein the binding substance specific for Aβ(x–$\geq$41) peptides has the specificity of a binding substance raised against peptide $NH_2$-Cys-NH—$CH_2$—$(CH_2)_5$—CO-GLMVGGVVIA-COOH (SEQ ID NO:4).

6. The method of claim 4 wherein the labeled detection binding substance for measuring the amount of Aβ(x–$\geq$41) peptides is specific for an epitope within the junction region of Aβ or is specific for an Aβ peptide whose amino-terminal amino acid is amino acid no. 1 of Aβ.

7. The method of claim 3 wherein the capture binding substance for measuring the amount of total Aβ is specific for an epitope within the junction region of Aβ and the capture binding substance for measuring the amount of the Aβ(x–$\leq$40) peptides is specific for Aβ(x–$\leq$40) peptides.

8. The method of claim 7 wherein the binding substance specific for an epitope within the junction region of Aβ has the specificity of a binding substance raised against the junction region of Aβ, and the binding substance specific for Aβ(x–$\leq$40) peptides has the specificity of a binding substance raised against the peptide $NH_2$-Cys-NH—$CH_2$—$(CH_2)_5$—CO-GLMVGGVV-COOH (SEQ ID NO:5).

9. The method of claim 7 wherein the labeled detection binding substance for measuring the amount of Aβ(x–$\leq$40) peptides has the specificity of a binding substance raised against the junction region, and the binding substance for measuring the amount of total Aβ has the specificity of a binding substance raised against a peptide with an Aβ amino acid sequence corresponding to amino acids within 1–5 of SEQ ID NO: 1 or amino acids 17–24 of SEQ ID NO: 1.

10. The method of claim 3 wherein the capture binding substance for measuring the amount of at least one of Aβ(x–$\geq$41) peptide, total Aβ or Aβ(x–$\leq$40) peptide is specific for an epitope within the junction region of Aβ.

11. The method of claim 2 comprising, before administration of the compound:

pulsing the culture with a radioactive label for protein;

chasing the culture without a radioactive label;

wherein the step of administering comprises administering the compound to the cell during the chase period; and the step of measuring the amount of the Aβ(x–$\geq$41) peptide, total Aβ or the Aβ(x–$\leq$40) peptide in a sample from the culture comprises:

contacting a sample from the culture with a binding substance specific for at least one Aβ(x–$\geq$41) peptide;

contacting a sample from the culture with a binding substance specific for total Aβ or at least one Aβ(x–$\leq$40) peptide; and determining the amount of radioactive label attached to the binding substances.

12. The method of claim 3 wherein the culture comprises primary human neurons or primary neurons from a transgenic mouse harboring the PDAPP construct.

13. The method of claim 2 wherein the culture comprises a 293 human kidney cell line, a human neuroglioma cell line, a human HeLa cell line, a primary endothelial cell line, a primary human fibroblast line, a primary lymphoblast line, human mixed brain cells, or a Chinese hamster ovary (CHO) cell line.

14. The method of claim 2 wherein the cell is a host cell transfected with a recombinant expression vector encoding a human APP.

15. The method of claim 14 wherein the human APP carries a Hardy mutation.

16. The method of claim 2 wherein the cell overproduces Aβ(x–$\geq$41) peptides.

17. The method of claim 2 wherein the sample is medium conditioned by the cell in culture.

18. The method of claim 2 further comprising the step of determining whether the compound is toxic to the cell.

19. The method of claim 1 wherein the Aβ(x–≧41) is Aβ(42).

20. The method of claim 19 comprising measuring total Aβ.

21. The method of claim 19 comprising measuring Aβ(x–≦40) wherein Aβ(x–≦40) is Aβ(40).

* * * * *